United States Patent
Weingand

(10) Patent No.: US 6,436,020 B1
(45) Date of Patent: Aug. 20, 2002

(54) ARTICLES OF MANUFACTURE AND METHODS FOR TREATING PAIN

(75) Inventor: Kurt William Weingand, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/371,707

(22) Filed: Aug. 9, 1999

(51) Int. Cl.$^7$ .............................................. A63B 22/14

(52) U.S. Cl. ........................ 482/148; 607/108; 607/112; 607/114; 602/14; 602/26

(58) Field of Search ................ 600/9, 15; 607/108–114; 482/148

(56) References Cited

U.S. PATENT DOCUMENTS

| | | | |
|---|---|---|---|
| 3,900,035 A | 8/1975 | Welch et al. ................ | 128/402 |
| 4,323,232 A | 4/1982 | Terpening .................... | 272/68 |
| 4,575,097 A | 3/1986 | Brannigan et al. .......... | 128/402 |
| 4,586,506 A | 5/1986 | Nangle ........................ | 128/403 |
| 4,671,267 A | 6/1987 | Stout ........................... | 128/156 |
| 4,688,572 A | 8/1987 | Hubbard et al. ............. | 128/402 |
| 4,742,827 A | 5/1988 | Lipton ......................... | 128/380 |
| 4,805,620 A | 2/1989 | Meistrell ..................... | 128/402 |
| 4,891,501 A | 1/1990 | Lipton ......................... | 219/527 |

(List continued on next page.)

FOREIGN PATENT DOCUMENTS

| | | | | |
|---|---|---|---|---|
| EP | 0 014 300 | 8/1980 | ............. | A61F/7/00 |
| WO | WO 98/29064 | 7/1998 | ............. | A61F/7/03 |
| WO | WO 98/29065 | 7/1998 | ............. | A61F/7/03 |
| WO | WO 98/29067 | 7/1998 | ............. | A61F/7/08 |

OTHER PUBLICATIONS

Greenberg, R.S. "The Effects of Hot Packs and Exercise on Local Blood Flow", Physical Therapy, vol. 52, No. 3, Mar. 1972, pp. 273–278.

Henricson, A.S., et al. "The Effect of Heat and Stretching on the Range of Hip Motion", The Journal of Orthopaedic and Sports Physical Therapy, vol. 6, No. 2, Sep./Oct,. 1984, pp. 110–115.

Price, D.D., et al. "Sensory–Affective Relationships Among Different Types of Clinical and Experimental Pain", Elsevier Science Publishers B.V. (Biomedical Division), Pain, 28 (1987) pp. 297–307.

Rodriguez, A.A., et al. "Therapeutic Exercise in Chronic Neck and Back Pain", Arch Phys. Med. Rehabil., vol. 73, Sep., 1992, pp. 870–875.

(List continued on next page.)

*Primary Examiner*—Michael A. Brown
*Assistant Examiner*—Lalita M. Hamilton
(74) *Attorney, Agent, or Firm*—Loy M. White

(57) ABSTRACT

The present invention is directed to articles of manufacture and methods for treating pain and increasing tissue healing and rehabilitation in patients suffering from injury and/or inflammation of the muscle and/or joints and/or skeletal system. The articles of manufacture include a source of topical heat and a set of instructions in association with the heat source. The set of instructions provides instructions for performing specific therapeutic exercises designed to develop or restore strength, endurance, and/or function to the body or part of the body of a human or animal afflicted with injury and/or inflammation. The methods include applying topical heat to the body or part of the body of a human or animal afflicted with injury and/or inflammation in combination with specific therapeutic exercises designed to develop or restore strength, endurance, and/or function to the body or part of the body of a human or animal afflicted with injury and/or inflammation.

24 Claims, 37 Drawing Sheets

U.S. PATENT DOCUMENTS

| | | | |
|---|---|---|---|
| 4,981,135 A | 1/1991 | Hardy | 128/402 |
| 5,000,176 A | 3/1991 | Daniel | 128/402 |
| 5,072,598 A | 12/1991 | Dibrell | 62/259.3 |
| 5,148,804 A | 9/1992 | Hill et al. | 128/402 |
| 5,179,942 A | 1/1993 | Drulias et al. | 128/101.1 |
| 5,211,949 A | 5/1993 | Salyer | 424/402 |
| 5,247,928 A | 9/1993 | Stilts, Jr. | 607/109 |
| 5,378,225 A | 1/1995 | Chatman, Jr. et al. | 602/19 |
| 5,398,667 A | 3/1995 | Witt | 126/263 |
| 5,415,222 A | 5/1995 | Colvin et al. | 165/46 |
| 5,415,624 A | 5/1995 | Williams | 602/21 |
| 5,496,357 A | 3/1996 | Jensen et al. | 607/108 |
| 5,496,358 A | 3/1996 | Rosenwald | 607/108 |
| 5,507,793 A | 4/1996 | Hodges | 607/109 |
| 5,534,021 A | 7/1996 | Dvoretzky et al. | 607/112 |
| 5,697,962 A | 12/1997 | Brink et al. | 607/108 |
| 5,728,057 A | 3/1998 | Ouellette et al. | 602/62 |
| 5,735,889 A | 4/1998 | Burkett et al. | 607/96 |
| 5,741,220 A * | 4/1998 | Brink | |
| 5,741,318 A | 4/1998 | Ouellette et al. | 607/108 |
| 5,837,005 A | 11/1998 | Viltro et al. | 607/112 |
| 5,904,710 A | 5/1999 | Davis et al. | 607/108 |
| 5,906,637 A | 5/1999 | Davis et al. | 607/108 |

OTHER PUBLICATIONS

Lentell G., et al. "The Use of Thermal Agents to Influence the Effectiveness of a Low–Load Prolonged Stretch", Research Study, JOSPT, vol. 16, No. 5, Nov., 1992, pp. 200–207.

Oddis, C.V. "New Perspectives on Osteoarthritis", The American Journal of Medicine, vol. 100 (suppl 2A) Feb. 26, 1996, pp. 2A–10S—15S.

McGuire, D.B. "Measuring Pain", Instruments for Clinical Health–Care Research, Second Edition, 1997, pp. 528–564.

Worthen, D.B. "Pratice Opportunities: Thermal Analgesic Devices: Effective Relief of Pain", Continuing Pharmacy Education, Jan., 1998, pp. 1–17.

Dowdy, P.A., et al. "Knee Arthritis in Active Individuals", The Physician and Sportsmedicine, vol. 26, No. 6, Jun., 1998, pp. 43–54.

Kinser, C., et al. "Stretching", Therapeutic Exercise, Foundations and Techniques, Third Edition, Mar. 1996, pp. 143–146, 164–166.

Michlovitz, S.L., et al. "Biophysical Principles of Heating and Superficial Heating Agents", Thermal Agents in Rehabilitation, Third Edition, 1996, pp. 107–116.

* cited by examiner

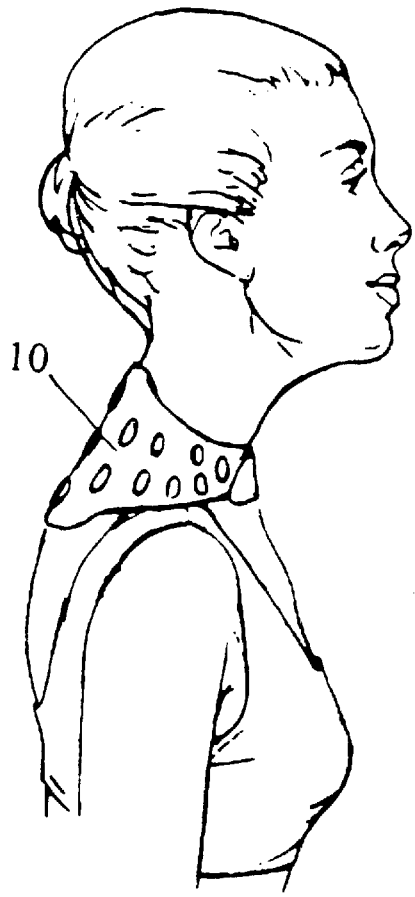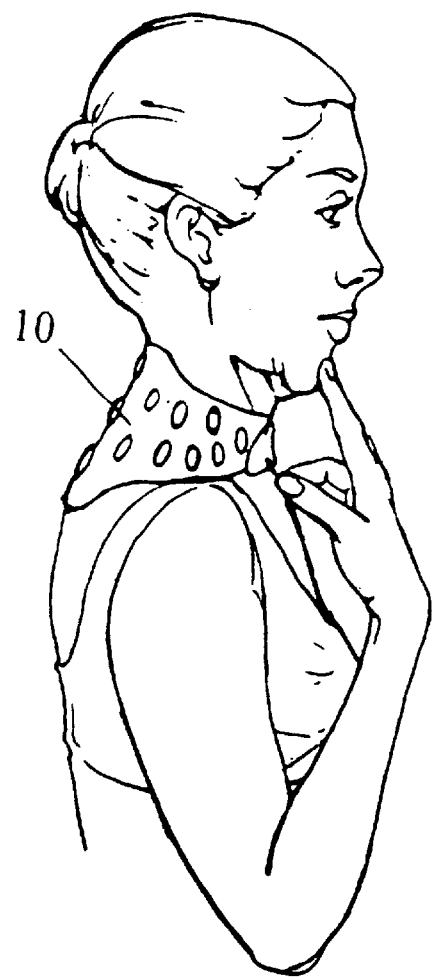
Fig. 1A
Fig. 1B

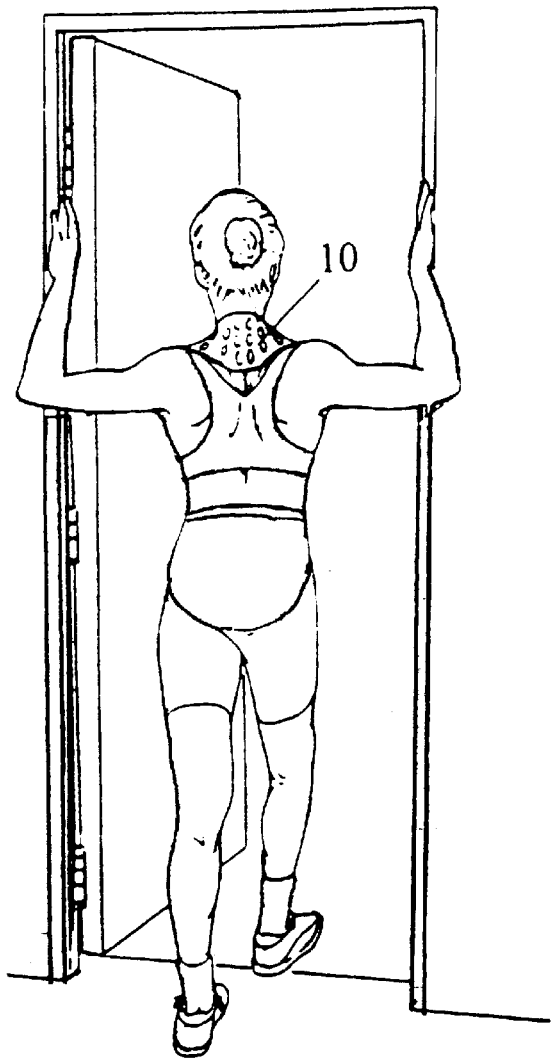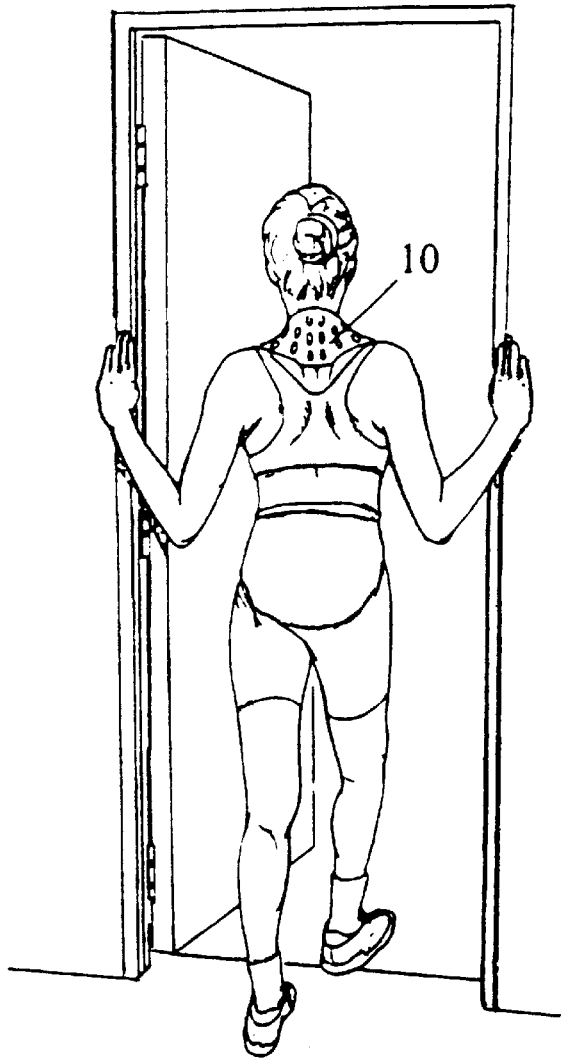
Fig. 5A                    Fig. 5B

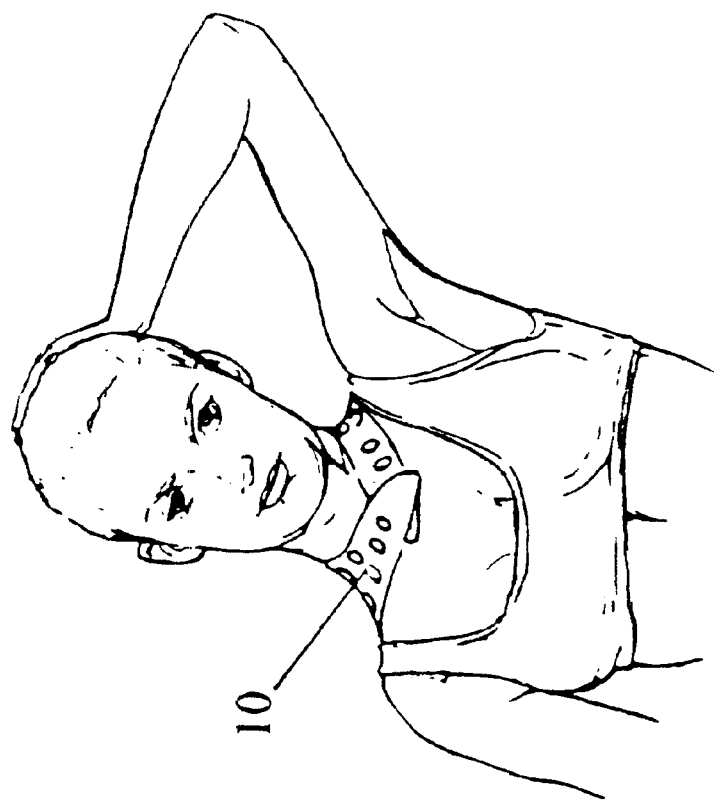
Fig. 7B
Fig. 7A

ARTICLES OF MANUFACTURE AND METHODS FOR TREATING PAIN

BACKGROUND

Pain at a site of injury and/or inflammation results from stimulation of pain receptors on peripheral sensory afferent nerve cell endings. Increased activity in these afferent nerve cells leads to release of chemical neurotransmitters at the gap junction between neurons in the dorsal horn of the spinal cord. The chemical neurotransmitters activate spinal cord neurons that leads to increased spinal reflex activity locally and the perception of pain in the brain.

Locally, the increased spinal reflex activity results in acute skeletal muscle contraction to minimize movement and the pain stimulus. If muscle contraction is persistent, a muscle spasm may develop, which may cause additional pain by physically stimulating pain receptors and decreasing tissue blood perfusion, which may lead to additional tissue injury from decreased oxygen availability and release of chemical mediators, such as bradykinin prostaglandins, lactic acid and potassium. The chemical mediators may increase vascular permeability by damaging blood vessels, which may lead to excess accumulation of fluid or blood in the tissues (edema and swelling) and additional physical stimulation of pain receptors. The chemical mediators may also stimulate the pain receptors directly.

The perception of pain in the brain in response to a pain stimulus may be enhanced by reactive changes in the spinal cord that increase sensory processing of pain signals, resulting in an exaggerated pain response, which may last for hours after the pain stimulus is stopped. The perception of pain in the brain typically leads to psychological effects manifested by characteristic behavior patterns and suffering.

Localized application of topical heat has been used for centuries to relieve pain and speed recovery from physical ailments. Topical heat stimulates thermoreceptors in superficial tissues which leads to inhibition of pain signals from afferent nerve cells to the dorsal horn of the spinal cord which decreases release of the chemical neurotransmitters at the gap junction between neurons, i.e., "gate control" theory of pain inhibition. This inhibition decreases the perception of pain in the brain, decreases efferent neurologic spinal reflex activity to skeletal muscle, and decreases muscular tone resulting in muscular relaxation.

Application of topical heat also increases vasodilatation of the skin, which increases blood flow at the site of inflammation and decreases the concentration of painful inflammatory mediators and provides nutrients for tissue repair and healing.

The use of topical heat alone, however, has not been completely satisfactory for treating/relieving body pain. Current topical heat sources restrict movement of the body. Proper positioning and efficient transfer of the thermal energy to the painful body region may not be maintainable during use, thereby limiting the user's movement and ability to participate in normal activities. Further, many of the heat sources such as hot towels, hot water bottles, hot packs, hand warmers, heating pads, heat wraps, and the like, employ reusable thermal packs containing, e.g., water and/or microwaveable gels, or electric current and are inconvenient to use on a regular and extended basis. Further, the thermal energy from these heat sources may not be properly provided over a long period of time, e.g., may not be immediately available when needed, may not be released in a consistent, controlled manner, and/or may cause burns to the skin.

Alternatively, therapeutic exercises have been used for treating body pain and rehabilitation of physical impairments. Exercise increases blood flow at the site of inflammation, decreases the concentration of inflammatory mediators, provides nutrients for tissue repair and healing, and enhances flexibility and mobility. This method of therapy, however, has also not been completely satisfactory for treating/relieving body pain. That is, the accompanying pain makes it difficult for patients to initiate and conduct the recommended therapeutic exercise or exercises, so patient compliance with therapeutic exercise programs is relatively low.

Based on the forgoing, there has been a long felt need for a topical composition, i.e., article of manufacture, and/or a satisfactory method for treating pain and increasing tissue healing in patients suffering from injury and/or inflammation of the muscle and/or joints and/or skeletal system . Historically, there has been no technology available that delivers topical heat therapy that can be used simultaneously while doing therapeutic exercise or exercises over an extended period of time. Therefore, the present invention provides articles of manufacture and methods for treating pain and increasing tissue healing in patients suffering from injury and/or inflammation of the muscle and/or joints and/or skeletal system by applying portable, topical heat to the body or part of the body afflicted with said injury and/or inflammation in combination with a specific therapeutic exercise or set of exercises designed to exercise the body or part of the body afflicted with injury and/or inflammation.

SUMMARY OF THE INVENTION

The present invention is directed to articles of manufacture and methods for treating pain and increasing tissue healing and rehabilitation in patients suffering from injury and/or inflammation of the muscle and/or joints and/or skeletal system. The articles of manufacture include a source of topical heat and a set of instructions in association with the heat source. In a preferred embodiment of the present invention the articles of manufacture include a container for holding, containing, or storing the topical heat source and set of instructions in association with the container. The set of instructions provides instructions for performing specific therapeutic exercises designed to develop or restore strength, endurance, and/or function to the body or part of the body of a human or animal afflicted with injury and/or inflammation. The methods include applying topical heat to the body or part of the body of a human or animal afflicted with injury and/or inflammation in combination with specific therapeutic exercises designed to develop or restore strength, endurance, and/or function to the body or part of the body of a human or animal afflicted with injury and/or inflammation.

These and other features, aspects, and advantages of the present invention will become evident to those skilled in the art from a reading of the present disclosure.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings in which like reference numerals identify identical elements and in which:

1. FIGS. 1–10 show preferred procedures for performing the exercise or exercises for relief of neck pain and proper positioning of a portable neck and/or upper back wrap comprising one or more thermal elements.

FIGS. 1A and 1B show a preferred procedure for performing the Chin Tuck Exercise.

FIG. 4 shows a preferred procedure for performing the Side Bending Stretch Exercise.

FIGS. 5A, 5B, and 5C show a preferred procedure for performing the Chest/Shoulder Stretch Exercise.

FIGS. 7A and 7B show a preferred procedure for performing the Resisted Side Bend (using hands) Exercise.

FIG. 8 shows an alternative position for performing a preferred procedure for performing the Resisted Side Bend (using an exercise ball) Exercise.

2. FIGS. 11–20 show preferred procedures for performing the exercise or exercises for relief of lower back pain and proper positioning of a portable lower back wrap comprising one or more thermal elements.

FIGS. 1A, 1B, and 1C show a preferred procedure for performing the Cat Stretch Exercise.

FIG. 13 shows a preferred procedure for performing the Alternate Extension (standing) Exercise.

FIG. 14 shows a preferred procedure for performing the Side Stretch Exercise.

FIG. 20 shows a preferred procedure for performing the Lower Abdominal Strengthening Exercise—"Bridge Position".

3. FIGS. 21–28 show preferred procedures for performing the exercise or exercises for relief of knee pain and proper positioning of a portable knee wrap comprising one or more thermal elements.

FIG. 22 shows a preferred procedure for performing the Alternate Quadriceps Stretch Exercise

FIG. 25 shows a preferred procedure for performing the Alternate Hamstring Stretch Exercise

FIG. 27 shows a preferred procedure for performing the Alternate Standing Squat Exercise.

FIG. 28 shows a preferred procedure for performing the Leg Lift Exercise.

4. FIGS. 29–34 show preferred procedures for performing the exercise or exercises for relief of body, abdominal, and/or menstrual pain and proper positioning of a portable body/abdomen patch comprising one or more thermal elements.

FIG. 31 shows a preferred procedure for performing the Buttock/Hip Stretch Exercise.

FIG. 34 shows a preferred procedure for performing the Lower Abdominal Strengthening Exercise—"Bridge Position".

DETAILED DESCRIPTION OF THE INVENTION

Figures 2A, 2B:
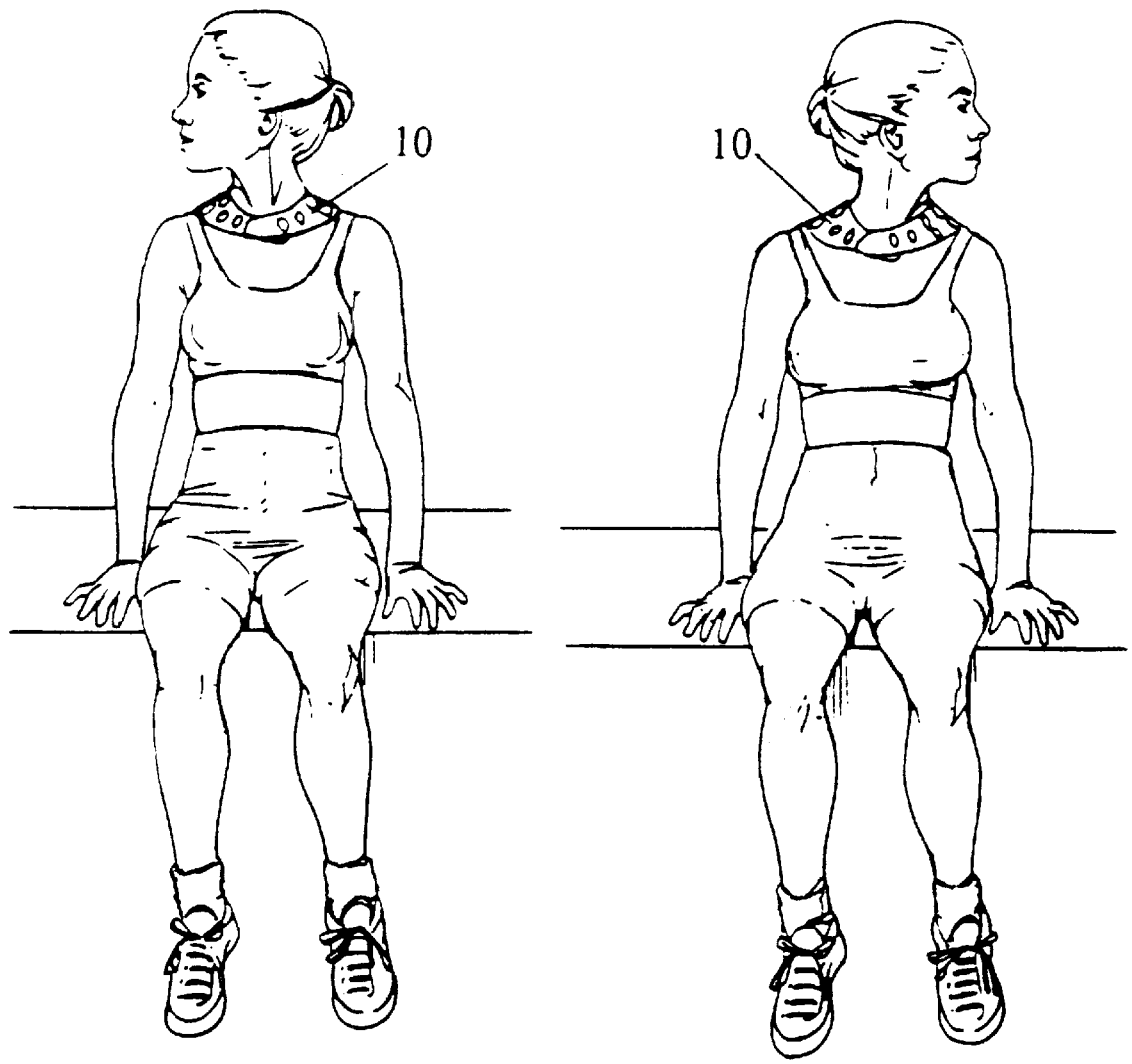
FIGS. 2A and 2B show a preferred procedure for performing the Head Rotation Exercise.

The present invention relates to a new physical therapy program that combines portable, topical heat treatment with a specific therapeutic exercise or set of exercises. This combination provides additive therapeutic benefits when is compared to either topical heat therapy or therapeutic exercise alone. The neurologic pain relief, relaxation of skeletal muscle, and increased flexibility provided by the topical heat treatment allows for increased joint movement and mobility for performing the specified therapeutic exercise or set of exercises, which leads to an additional increase in tissue blood flow that will enhance healing. This combination physical therapy program uniquely allows for additive implementation of the therapeutic benefits of topical heat and therapeutic exercise to enhance rehabilitation.

The embodiments of the present invention include articles of manufacture having a topical heat source comprising a portable body or body part wrap or patch having one or more thermal elements for applying thermal energy to specific areas of the user's body or body part and a set of instructions in association with the heat source for enabling a human in need of treating acute, recurrent, and/or chronic pain, including homotopic, heterotopic, muscular, and/or skeletal pain, to perform a specific exercise or set of exercises designed to promote muscular strength, endurance, and flexibility while wearing said topical heat source. In a preferred embodiment of the present invention, the articles of manufacture include a container for containing a topical heat source and a set of instructions, a topical heat source, and a set of instructions in association with the container. The embodiments of the present invention further include methods for treating acute, recurrent, and/or chronic pain, including homotopic, heterotopic, muscular, and/or skeletal pain, of a human or animal suffering such pain comprising topically applying thermal energy and physical support to the specific areas of the body of a human or animal suffering such pain, in combination with a specific exercise or set of exercises designed to promote muscular strength, endurance, and flexibility.

Herein, "comprising" means that other steps and/or other ingredients which do not affect the end result can be added. This term encompasses the terms "consisting of" and "consisting essentially of".

Herein, "in association with", means the instructions are either directly printed on the topical heat source and/or container or presented in a different manner including, but not limited to, a brochure, print advertisement, electronic advertisement, and/or verbal communication, so as to communicate the set of instructions to a consumer of the articles of manufacture. A more comprehensive description is included in the Detailed Description of the Invention.

Herein, "body", means the head, neck, trunk (including the thorax and abdomen), and extremities (including arms, hands, hips, legs, feet) of a human or animal.

Herein, "pain", means an unpleasant sensation of the body or part of the body typically characterized by localized physical discomfort, such as pricking, throbbing, and/or aching, induced by a noxious stimulus associated with actual or potential tissue damage, such as disease and/or injury.

Herein, "acute pain", means pain which is typically of short and sharp course.

Herein, "chronic pain", means pain which is typically of long duration, i.e., denoting a disease of slow progression and long continuance.

Herein, "recurrent pain", means pain which is typically acute, but may also include chronic, and reoccurs after an intermission or remission.

Herein, "muscular pain", means acute, chronic, or recurrent pain which typically is associated with the skeletal muscle(s) and/or smooth muscle(s) of the body or a part of the body of a human or animal.

Herein, "skeletal pain", means acute, chronic, or recurrent pain which typically is associated with the bony framework of the body or part of the body of a human or animal which includes the bones, ligaments, and cartilages.

Herein, "homotopic pain" means acute, chronic, or recurrent pain which typically is felt at the point of the body or part of the body of disease or injury.

Herein, "heterotopic pain", means acute, chronic, or recurrent pain which typically is perceived as coming from an area of the body or part of the body remote from its actual origin and may include pain associated with the viscera of the body or part of the body, such as menstrual pain. Also known as "referred pain".

Herein, "container", means any means for holding, containing, and/or storing the components of the embodiments of the present invention. While there are no particular limitations to the type of container which may be used, suitable containers may include, but are not limited to, boxes, bags, envelops, pouches, bottles, jars, cartons, packets, shrink wrap, and the like.

Herein, "topical heat source", means those topical heat sources which include, but are not limited to, hot towels, hot water bottles, hot packs, hand warmers, heating pads, heating patches, heat wraps, and the like. While there are no particular limitations to the means by which the thermal energy may be generated by the topical heat source, the source must be portable, provide a consistent and controlled thermal energy for an extended period of time, direct the thermal energy to where it has the most therapeutic benefit, and provide efficient and effective heat coverage by having excellent conformity with the user's body and/or body part without substantially hindering movement.

Herein, "topically applied heat", means heat or warmth that is applied to the surface or skin of the body or part of the body of a human or animal.

Herein, "thermal", means of, relating to, or caused by heat and may be used interchangeably with the term "heat".

Herein, "maintaining skin temperature", means maintaining a sustained skin temperature of from about 32° C. to about 50° C. for from about fifteen minutes to about eight hours. Fluctuations in actual skin temperature may occur for short periods of time, e.g., from about one minute to about one hour, as long as the skin temperature remains within the temperature range described above.

Herein, "exercise", means the controlled movement(s) of the body or part of the body of a human or animal to develop or restore strength, endurance, and/or function to the body or part of the body of a human or animal.

Herein, "therapeutic exercise", means exercise to improve bodily function(s), relieve symptoms, or maintain a state of well being of a human or animal.

All cited references are incorporated herein by reference in their entireties, unless otherwise specified. Citation of any reference is not an admission regarding any determination as to its availability as prior art to the claimed invention.

All percentages are by weight of total composition unless specifically stated otherwise.

All ratios are weight ratios unless specifically stated otherwise.

Articles of Manufacture

The articles of manufacture of the present invention provide a treatment for the relief of acute, recurrent, and/or chronic pain, including homotopic, heterotopic, muscular, and/or skeletal pain and include: 1) a topical heat source comprising a portable body or body part wrap or patch having one or more thermal elements for applying thermal energy and physical support to specific areas of the user's body or body part and 2) a set of instructions in association with the topical heat source for enabling a human to perform specific therapeutic exercises designed to develop or restore strength, endurance, and/or function to the body or part of the body of a human or animal afflicted with injury and/or inflammation while wearing said topical heat source. In a preferred embodiment of the present invention, the articles of manufacture include: 1) a container for holding, containing, and/or storing the components of the embodiments of the present invention, 2) a topical heat source comprising a portable body or body part wrap or patch having one or more thermal elements for applying thermal energy and physical support to specific areas of the user's body or body part, and 3) a set of instructions in association with the container for enabling a human to perform specific therapeutic exercises designed to develop or restore strength, endurance, and/or function to the body or part of the body of a human or animal afflicted with injury and/or inflammation while wearing said topical heat source.

I. Container

The articles of manufacture of the present invention include a container. Suitable containers for the present articles of manufacture include, but are not limited to, boxes, bags, envelops, pouches, bottles, jars, cartons, packets, shrink wrap, and the like.

II. Topical Heat Source

The articles of manufacture of the present invention further include a topical heat source. Some examples of these topical heat sources include, but are not limited to, those described in U.S. Pat. Nos.: 1,491,539; 2,002,673; 2,547,886; 2,562,121; 2,602,302; 3,463,161; 3,900,035; 3,976,049; 3,980,070; 4,095,583; 4,114,591; 4,205,685; 4,282,005; 4,331,731; 4,366,804; 4,462,224; 4,522,190; 4,516,564; 4,573,447; 4,575,097; 4,586,506; 4,671,267; 4,688,572; 4,742,827; 4,753,241; 4,756,299; 4,805,620; 4,860,748; 4,886,063; 4,891,501; 4,981,135; 5,000,176; 5,025,777; 5,046,479; 5,072,598; 5,148,804; 5,179,944; 5,190,033; 5,211,949; 5,247,928; 5,275,156; 5,342,412; 5,534,021; 5,366,491; 5,366,492; 5,378,225; 5,395,399; 5,398,667; 5,415,222; 5,496,357; 5,496,358; 5,507,793; 5,605,144; 5,649,914; 5,697,962; and Re. 32,026. It is preferred, for embodiments of the present invention, to use the portable, disposable, heat wraps and/or patches described in U.S. Pat. Nos.: 5,674,270; 5,728,057; 5,728,058; 5,728,146; 5,735,889; 5,741,318; 5,837,005; 5,860,945; 5,904,710; 5,906,637; 5,925,072; 6,019,782; 6,048,326; 6,074,413; 6,096,067; 6,102,937; 6,123,717; D403,779; D403,778; D407,824; D408,923; D407,822; D380,051; and D407,823.

The above named patents and/or applications related to the preferred embodiments of the present invention are assigned to The Procter & Gamble Co., Cincinnati, Ohio.

Preferred portable, disposable, thermal wraps include knee wraps, joint wraps, neck wraps, back wraps, body wraps, body patches, and multipurpose wraps currently marketed under the brand name of ThermaCare® HeatWraps by The Procter & Gamble Co., Cincinnati, Ohio.

Briefly, the ThermaCare® thermal knee and joint wraps are typically disposable and include at least one piece of flexible material having an outer surface, a body-facing surface, a first end, a second end, an elastic portion stretchable along a longitudinal axis of the piece of flexible material, a reclosable fastening system, one or more thermal packs comprising a plurality of heat cells, and a length great enough to encircle a user's knee or elbow such that the first and second ends overlap. The piece of flexible material further includes an upper strap potion and a lower strap portion, each having at least one hook member which can be independently fastened to loop members on the outer surface and the body-facing surface. Preferably, the upper and lower strap portions contain at least one elastic portion. That is, upper and lower strap portions preferably exhibit elastic behavior when stretched in a direction parallel to the longitudinal axis of the piece of flexible material. Upon application of the wrap, the first end of the upper strap portion encircles behind the user's leg or arm above the knee or elbow and the first end of the lower strap portion encircles behind the user's leg or arm below the knee or elbow. The upper and lower strap portions allow easier application and differential tensioning of the wrap during use. The piece of flexible material also includes a body portion having an aperture therein intended to be aligned with the user's patella or olecranon to establish a convenient locating point for wrapping the knee or joint wrap around the user's knee or elbow and at least one slit extending substantially along the longitudinal axis from the aperture for enabling the piece of flexible material to stretch transverse to the longitudinal axis at the aperture in order to accommodate bending of the user's knee or elbow.

The ThermaCare® thermal back wraps and body wraps are typically disposable and include at least one substantially rectangular piece of flexible material having an outer surface, a body-facing surface, a first end, a second end, an elastic portion stretchable along a longitudinal axis of the piece of flexible material, a reclosable fastening system, one or more thermal packs comprising a plurality of heat cells, and a length great enough to encircle a user's torso or body part such that the first and second ends overlap.

The ThermaCare® thermal neck wraps are typically disposable and include at least one substantially U-shaped piece of flexible material having a first arm portion, a second arm portion, a central body portion therebetween, one or more thermal packs comprising a plurality of heat cells, a body-facing surface, and an opposing outer surface, such that when the neck wrap is placed on a user, the central body portion is centered at the user's upper back and lower neck. First and second arm portions lay over the user's shoulders toward the user's chest.

The ThermaCare® thermal body patches and multipurpose wraps are typically disposable and include a substantially planar unified laminate structure having a first side, a second side, and one or more thermal packs comprising a plurality of heat cells. The laminate structure further includes a means for providing oxygen to the plurality of heat cells, and a means for releasably attaching the thermal body pad to an inside portion of a user's clothing or skin.

The ThermaCare® HeatWraps described above further include one or more individual heat cells or thermal packs. The individual heat cells, ThermaCells®, have specific physical dimensions and fill characteristics and preferably include a mixture of powdered iron, powdered carbon, water, and salt, which when exposed to oxygen, provide a controlled and sustained temperature and which reach their operating temperature range quickly. The heat cells are described in U.S. Pat. No. 5,918,590 and pending U.S. patent application Ser. No. 08/623,752, both of which are assigned to The Procter & Gamble Co., Cincinnati, Ohio. The thermal packs include a unified structure having at least one continuous layer of material and a plurality of heat cells spaced apart and fixed within or to the unified structure of the thermal pack. The thermal packs are described in pending U.S. patent application Ser. Nos. 08/777,853 and 08/984,009, both of which are assigned to The Procter & Gamble Co., Cincinnati, Ohio.

The ThermaCare® HeatWraps have thermal element, i.e., heat cell, pattern and alignment and position maintenance features that directs the thermal energy to where it has the most therapeutic benefit, provide efficient and effective heat coverage by having excellent conformity with the user's neck, back, body, knee, elbow, arm and/or leg, and can be worn under outer clothing with minimal visibility.

III. Set of Instructions

The articles of manufacture of the present invention still further include a set of instructions in association the heat source and/or the container which includes the instructions to enable a human in need of relief from acute, recurrent, and/or chronic pain, including homotopic, heterotopic, muscular, and/or skeletal pain, to perform a specific therapeutic exercise or set of exercises designed to promote muscular strength, endurance, flexibility, and increase tissue healing and rehabilitation, while wearing at least one of the above-described topical heat sources, preferably the ThermaCare® HeatWraps.

The set of instructions of the present articles of manufacture may be a brochure or print advertisement enclosed within the topical heat source and/or container, wherein the brochure or print advertisement includes instructions to perform the therapeutic exercise or set of exercises, appropriate for the specific afflicted body part, described herein and/or instructions directing the consumer to dial a specific telephone number wherein the instructions to perform the therapeutic exercise or set of exercises, appropriate for the specific afflicted body part, described herein are presented by verbal communication, and/or instructions directing the consumer to a specific computer internet website wherein the instructions to perform the therapeutic exercise or set of exercises, appropriate for the specific afflicted body part, described herein are displayed as an electronic advertisement. Alternatively, the set of instructions to perform the therapeutic exercise or set of exercises, appropriate for the specific afflicted body part, described herein may be directly printed on the topical heat source and/or container, and/or instructions may be directly printed on the topical heat source and/or the container directing the consumer to dial a specific telephone number wherein the set of instructions to perform the therapeutic exercise or set of exercises, appropriate for the specific afflicted body part, described herein is presented by verbal communication, and/or instructions may be directly printed on the topical heat source and/or the container directing the consumer to a specific computer internet website wherein the set of instructions to perform the therapeutic exercise or set of exercises, appropriate for the specific afflicted body part, described herein is displayed as an electronic advertisement.

Therapeutic Exercises

Referring now to FIGS. 1–34, the following exercises promote muscular strength, endurance, flexibility, and increase tissue healing and rehabilitation to a human in need of relief from acute, recurrent, and/or chronic pain, including homotopic, heterotopic, muscular, and/or skeletal pain, due to, but not limited to, injury and/or inflammation of the user's neck, back, body, knee, elbow, arm and/or leg. It is a preferred embodiment of the present invention that the therapeutic exercise or set of exercises be performed while applying topical heat to the afflicted body part. It is a more preferred embodiment of the present invention that the exercise or exercises be performed while the user is wearing one or more above-described ThermaCare® HeatWraps, appropriately selected for the specific afflicted body part.

I. Exercises for Neck Pain

The following exercises, shown in FIGS. 1–10, promote muscular strength, endurance, flexibility, and increase tissue healing and rehabilitation to a human in need of relief from acute, recurrent, and/or chronic pain, including homotopic, heterotopic, muscular, and/or skeletal pain, due to, but not limited to, injury and/or inflammation of the user's neck and/or upper back. All of the following exercises are to be performed according the Methods of Treating Pain, described below. That is, the user is instructed to apply topical heat, i.e., from about 32° C. to about 50° C., to the afflicted area of the body from about thirty minutes to about six hours prior to beginning the therapeutic exercise or set of exercises, to completion to about six hours after completion of the therapeutic exercise or set of exercises. Preferably the user performs the following exercises while wearing a thermal neck wrap 10, preferably the ThermaCare® HeatWrap for the neck.

A. Postural Exercise

1. Chin Tuck (FIG. 1)

Starting position: sitting tall, shoulders back, chest lifted, feet shoulder-width apart.

a. Stick chin out, mouth closed (FIG. 1A).

b. Place two fingers on chin and guide it gently back toward throat. Keep eyes straight ahead. Avoid tilting head forward (FIG. 1B).

c. Hold chin in tucked position for 20 seconds, then relax.

d. Repeat two times for a total of three repetitions.

B. Neck Flexibility Exercises

1. Head Rotation (FIG. 2)

Starting position: sitting tall, shoulders back, chest lifted, feet shoulder-width apart.

a. Turn head slowly to the right as far as is comfortable, keeping chin tucked in (FIG. 2A).

b. Hold 20 seconds.

c. Rotate head back to center position.

d. Then turn head to the left as far as is comfortable, keeping chin tucked in (FIG. 2B).

e. Hold 20 seconds.

f. Turn back to center and relax.

g. Repeat two times for a total of three repetitions.

2. Flexing/Extending the Neck(FIG. 3)

Figures 3A, 3B:
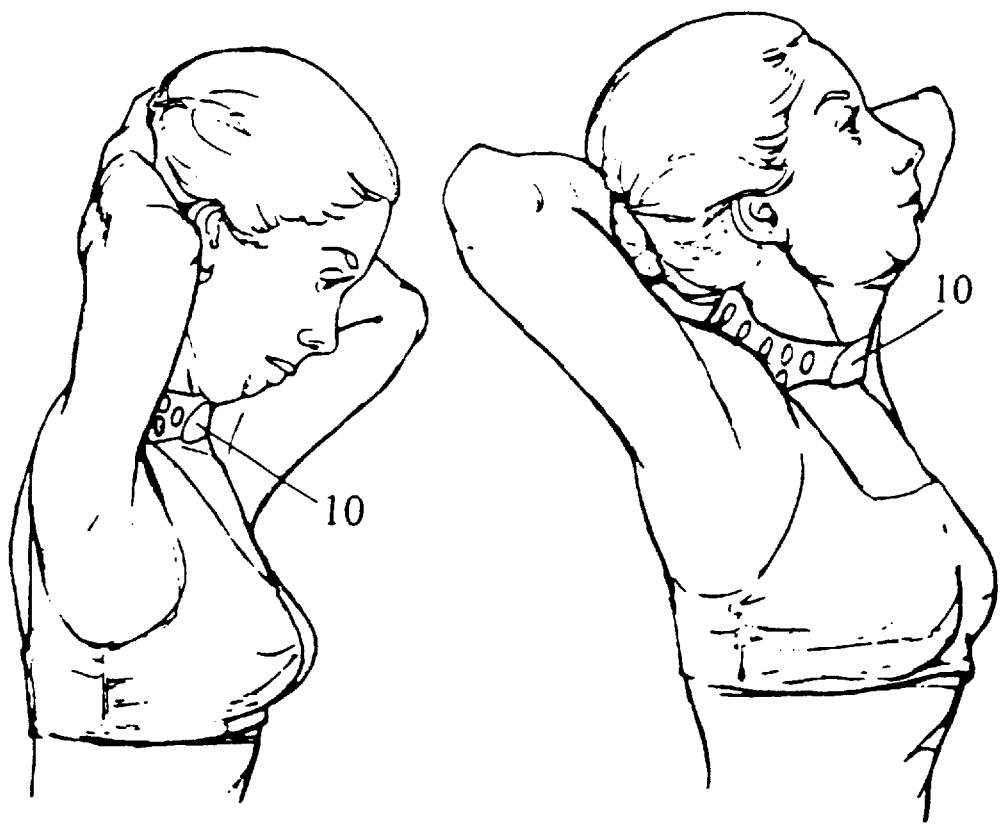
FIGS. 3A and 3B show a preferred procedure for performing the Flexing/Extending the Neck Exercise.

Starting position: sitting tall, shoulders back, chest lifted, feet shoulder-width apart.

a. Clasp hands behind head.

b. Tuck chin in.

c. Move chin toward chest as far as is comfortable. Do not pull on head with hands (FIG. 3A).

d. Hold 20 seconds.

e. Return to sing position, keeping hands clasped behind head as in step a.

f. Push head backward as far as is comfortable, lifting chest toward the ceiling and gently pushing elbows outward (FIG. 3B).

g. Hold 20 seconds, then relax and return to starting position.

h. Repeat two times for a total of three repetitions.

Figure 4:
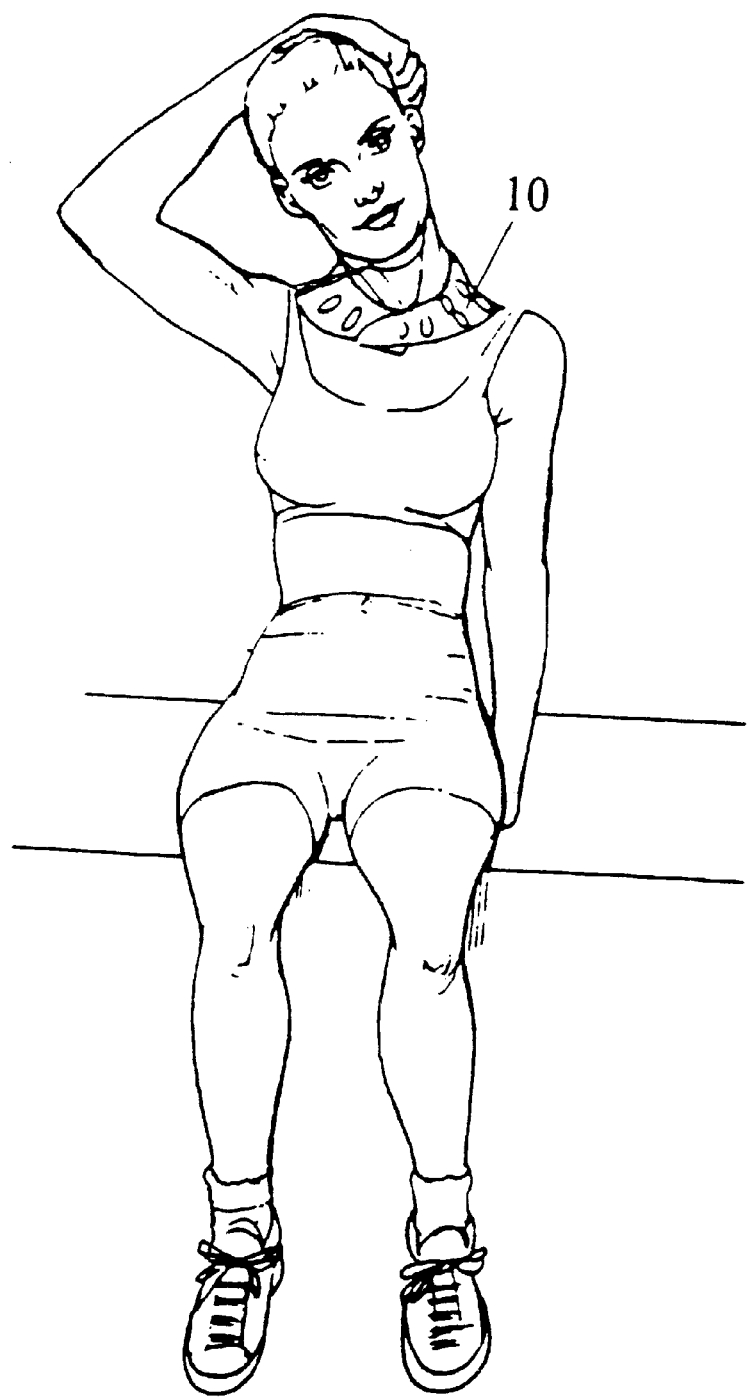

3. Side Bending Stretch (FIG. 4)

Starting position: sitting tall in a chair, shoulders back, chest lifted, feet shoulder-width apart.

a. Grab the seat of the chair with left hand.

b. Place right hand over the top of head above left ear.

c. Slowly tilt head to the right such that right ear approaches right shoulder. Keep chin tucked in (FIG. 4).

d. Hold five seconds, then slowly tilt head more to the right such that right ear is closer to right shoulder.

e. Hold five seconds, then relax and return to starting position.
f. Repeat steps a–e three times, each time going to the full extent of comfort range.
g. Reverse hand positions (left hand over the top of head above right ear) and repeat steps a–f on the left side.
h. Repeat two times for a total of three repetitions.

4. Chest/Shoulder Stretch (FIG. 5)

Starting position: standing in a doorway with forearms braced along the sides of the doorway and elbows at shoulder level (FIG. 5A).
 a. Tuck chin in and look forward.
 b. Leaving arms in place, step slowly through the doorway, squeezing shoulder blades together and downward.
 c. Hold for 20 seconds, then relax and return to starting position.
 d. Repeat two times for a total of three repetitions.

Figure 5C:
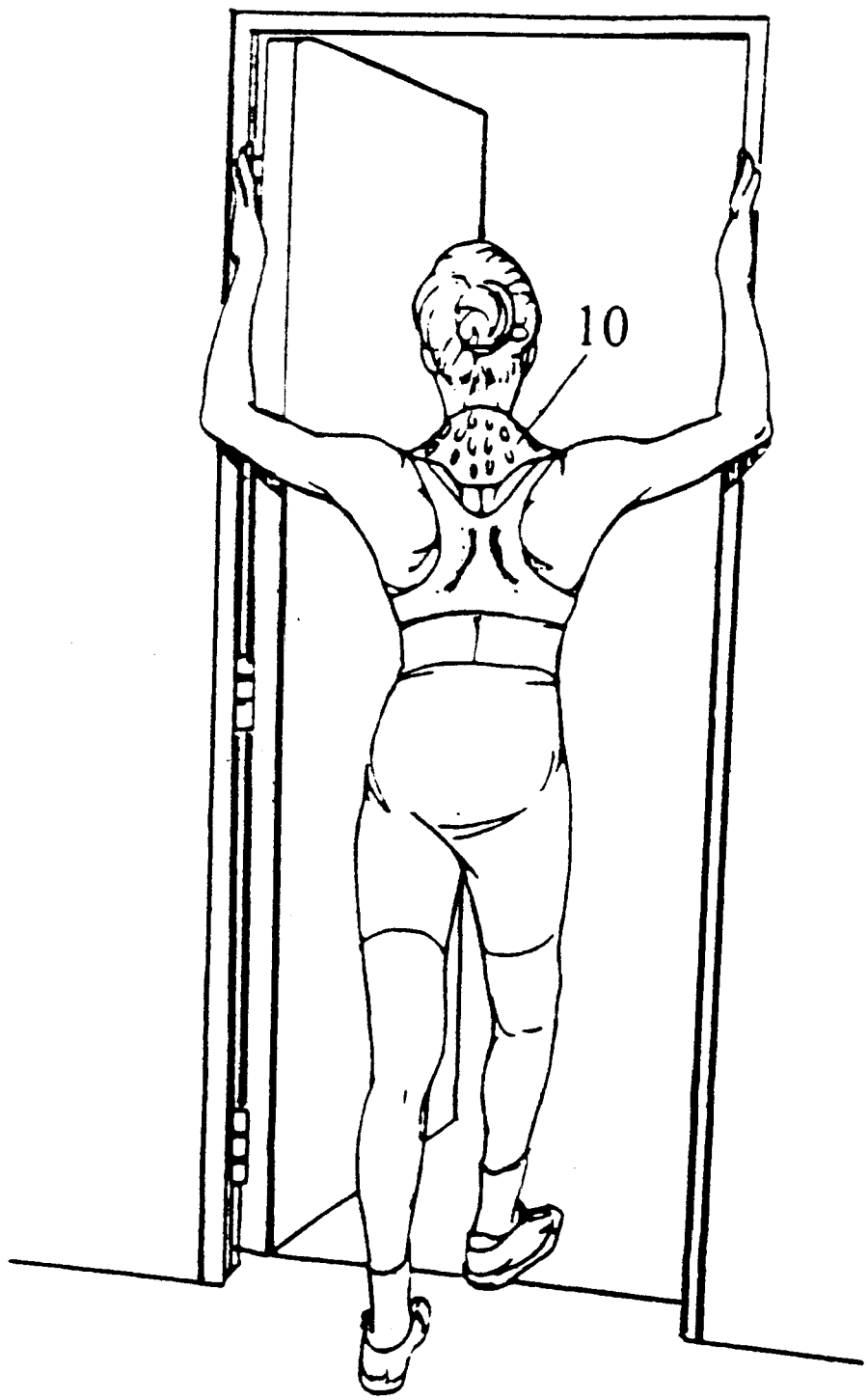

In the alternative, this exercise may be done with elbows below shoulder level (FIG. 5B) or elbows above shoulder level (FIG. 5C).

5. Shoulder Squeeze (FIG. 6)

Starting position: standing or sitting tall, shoulders back, chest lifted, feet shoulder-width apart.
 a. Tuck chin in.
 b. Move shoulders backward to squeeze shoulder blades together and downward. If sitting, grab the back of a chair during the squeeze (FIG. 6A).
 c. Hold for 20 seconds, then relax and return to starting position.
 d. Repeat two times for a total of three repetitions.

Figure 6A:
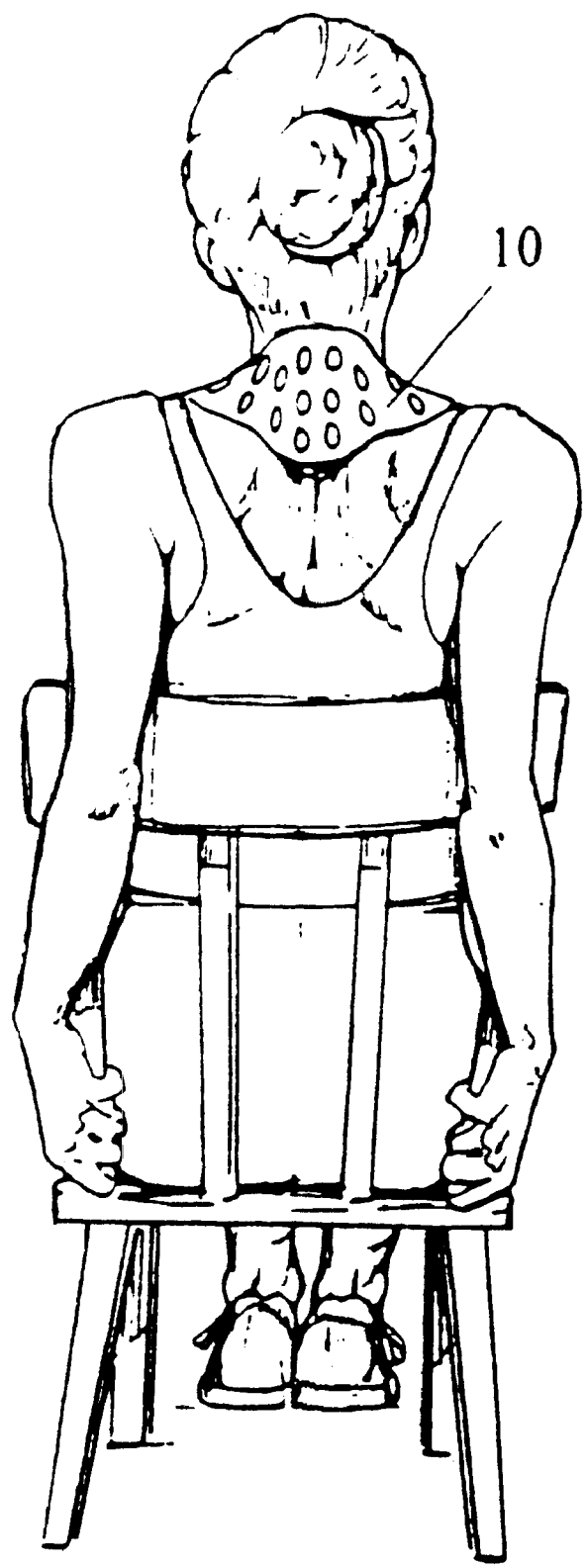
FIG. 6A shows a preferred procedure for performing the Shoulder Squeeze Exercise.
Figure 6B:
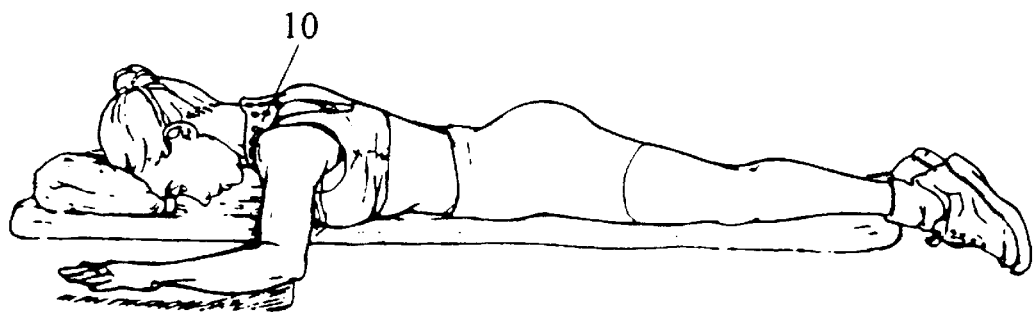
FIGS. 6B and 6C show two alternative positions for performing a preferred procedure for performing the Shoulder Squeeze Exercise.
Figure 6C:
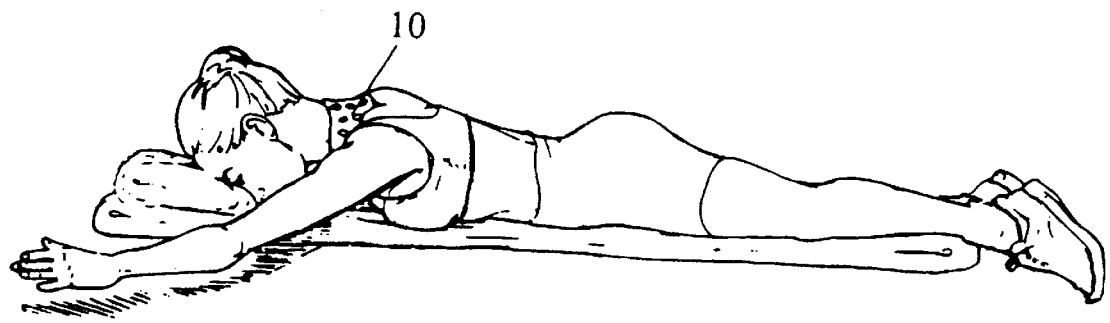

In the alternative, this exercise may be done lying on stomach with arms in the "goal-post" position (FIG. 6B), then moving arms forward to the "Y" position, keeping hands about 1 inch off the flat horizontal surface (FIG. 6C). Rest forehead on a towel on the flat horizontal surface.

C. Neck Strengthening Exercises

1. Resisted Side Bend (FIG. 7)

Starting position: standing or sitting tall, shoulders back, chest lifted, feet shoulder-width apart.
 a. Tuck chin in.
 b. Place right hand on the right side of head.
 c. Push head against hand (FIG. 7A).
 d. Hold 10 seconds, then relax and return to starting position.
 e. Repeat two times for a total of three repetitions, then reverse hand positions (left hand on the left side of head) and repeat steps a–d on the left side (FIG. 7B).

Figure 8:
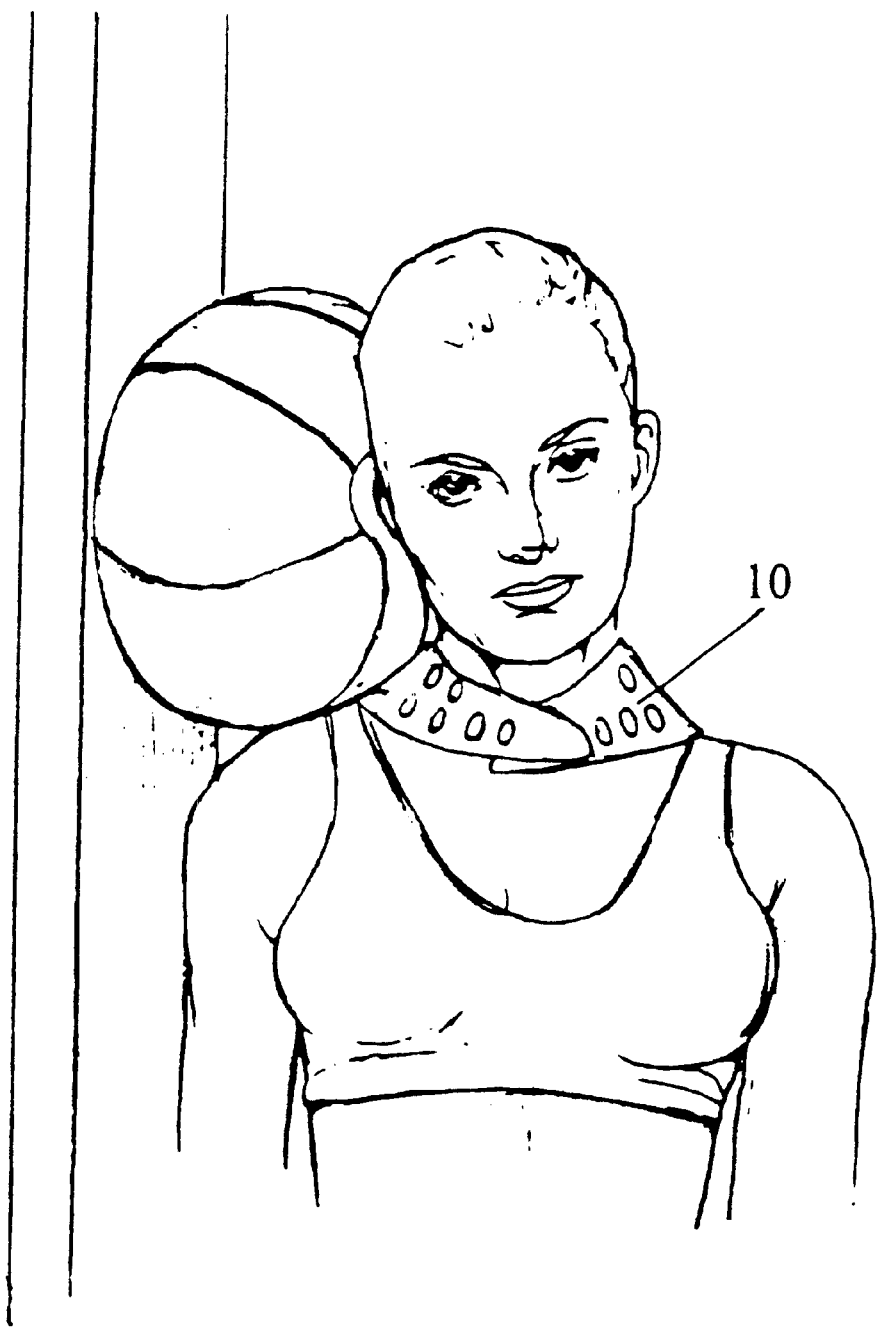
Figure 9A:
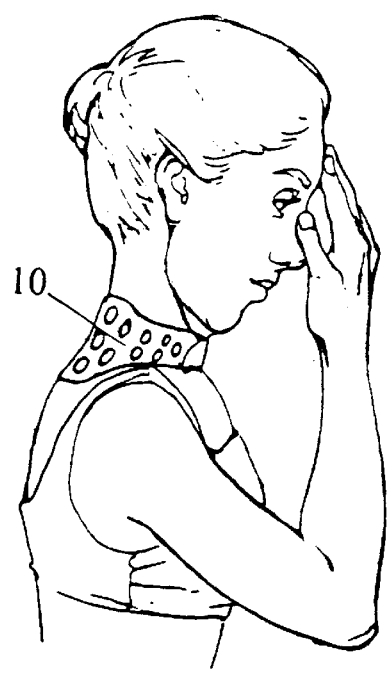
FIG. 9A shows a preferred procedure for performing the Resisted Flexion Exercise.
Figure 9B:
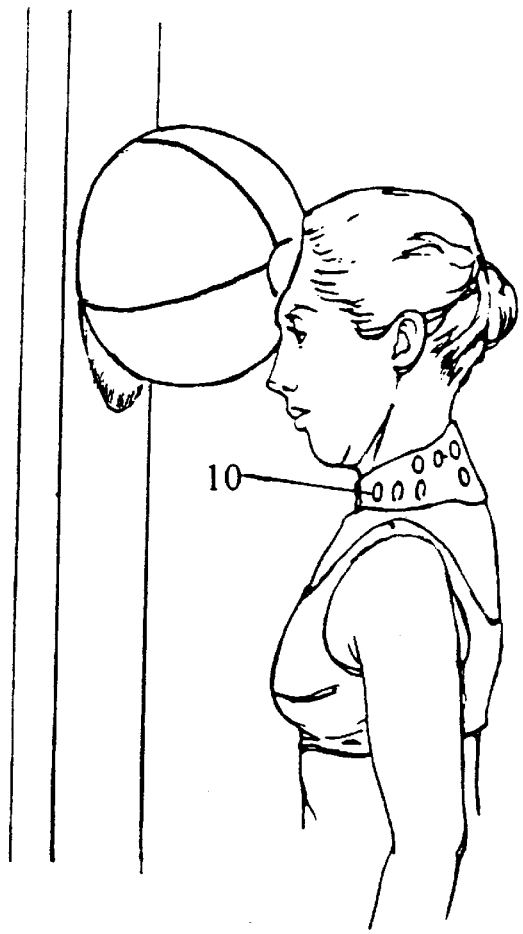
FIG. 9B shows an alternative position for performing a preferred procedure for performing the Resisted Flexion (using an exercise ball) Exercise.
Figure 10A:
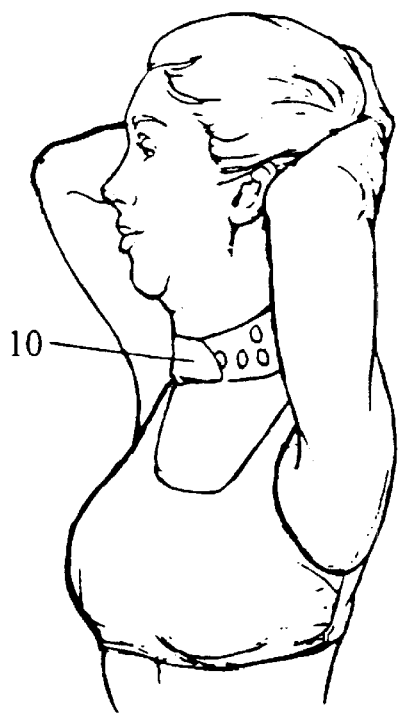
FIG. 10A shows a preferred procedure for performing the Resisted Extension Exercise.
Figure 10B:
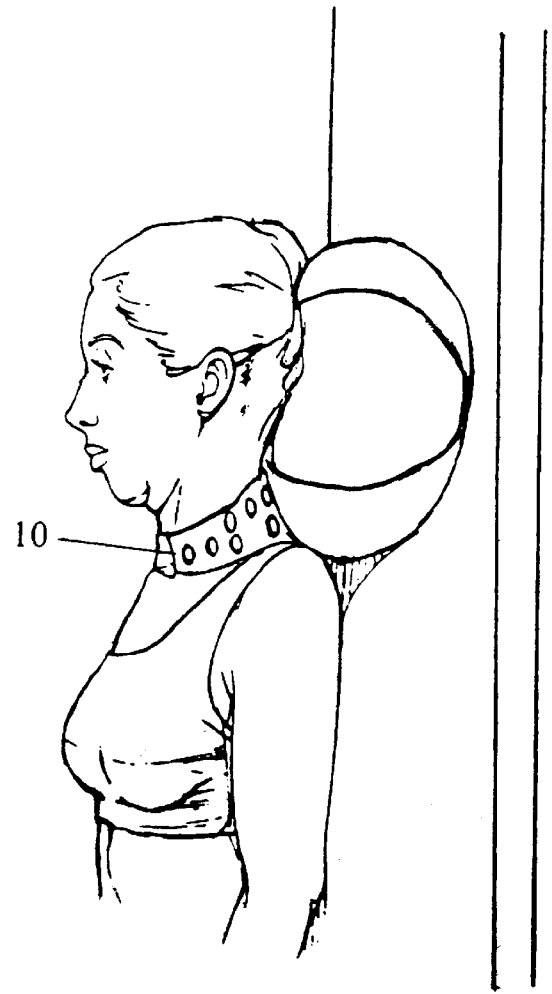
FIG. 10B shows an alternative position for performing a preferred procedure for performing the Resisted Extension (using an exercise ball) Exercise.

2. Alternate Resisted Side Bend (FIG. 8)

Starting position: standing tall, with right side of body to a vertical surface and an exercise ball placed snugly between head and the vertical surface.
 a. Tuck chin in.
 b. Push head to the right against the exercise ball.
 c. Hold 10 seconds, then relax and return to starting position.
 d. Repeat two times for a total of three repetitions, then reverse positions (left side of body to the vertical surface) and repeat steps a–c on the left side.

3. Resisted Flexion (FIG. 9)

Starting position: standing or sitting tall, shoulders back, chest lifted, feet shoulder-width apart.
 a. Tuck chin in.
 b. With one hand, press fingertips against forehead.
 c. Push head forward against fingers (FIG. 9A).
 d. Hold 10 seconds, then relax and return to starting position.
 e. Repeat two times for a total of three repetitions.

4. Alternate resisted flexion FIG. 9)

Starting position: standing facing a vertical surface, with an exercise ball placed snugly between forehead and the vertical surface, feet shoulder-width apart.
 a. Tuck chin in.
 b. Push forehead against the ball (FIG. 9B).
 c. Hold 10 seconds, then relax and return to starting position.
 d. Repeat two times for a total of three repetitions.

5. Resisted Extension (FIG. 10)

Starting position: standing or sitting tall, shoulders back, chest lifted, feet shoulder-width apart
 a. Put hands behind head, fingers interlaced.
 b. Tuck chin in.
 c. Push head backward against hands (FIG. 10A).
 d. Hold 10 seconds, then relax and return to starting position.
 e. Repeat two times for a total of three repetitions.

6. Alternate Resisted Extension (FIG. 10)

Starting position: standing with back to a vertical surface, an exercise ball placed snugly between the back of head and the vertical surface, feet shoulder-width apart.
 a. Tuck chin in.
 b. Push head against the ball (FIG. 10B).
 c. Hold 10 seconds, then relax and return to starting position.
 e. Repeat two times for a total of three repetitions.

II. Exercises for Lower Back Pain

The following exercises, shown in FIGS. 11–20, promote muscular strength, endurance, flexibility, and increase tissue healing and rehabilitation to a human in need of relief from acute, recurrent, and/or chronic pain, including homotopic, heterotopic, muscular, and/or skeletal pain, due to, but not limited to, injury and/or inflammation of the user's lower back. All of the following exercises are to be performed according the Methods of Treating Pain, described below. That is, the user is instructed to apply topical heat, i.e., from about 32° C. to about 50° C., to the afflicted area of the body from about thirty minutes to about six hours prior to beginning the therapeutic exercise or set of exercises, to completion to about six hours after completion of the therapeutic exercise or set of exercises. Preferably the user performs the following exercises while wearing a thermal back wrap 20, preferably the ThermaCare® HeatWrap for the back.

A. Low Back Mobility Exercises

1. Cat Stretch (FIG. 11)

Figure 11A:
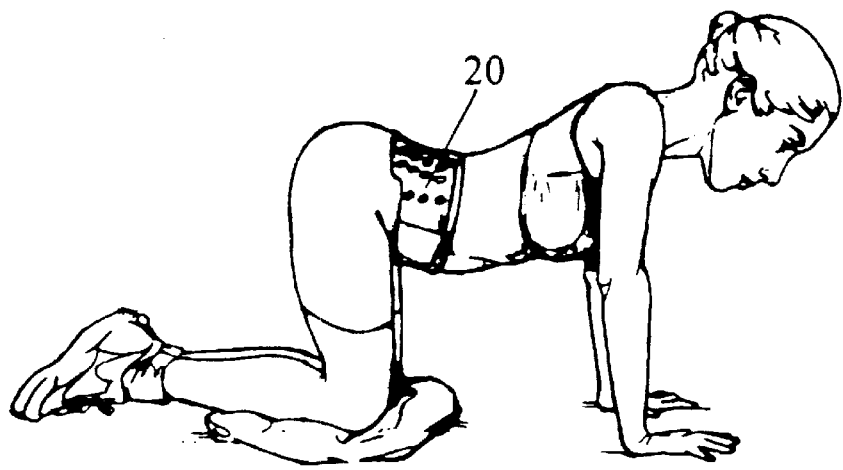
Figure 11B:
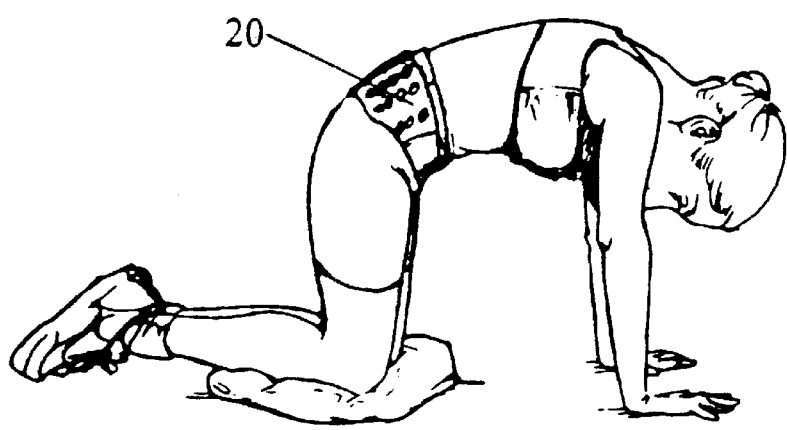
Figure 11C:

Starting position: on hands and knees on a flat horizontal surface, hands under shoulders, knees under hips, feet relaxed, eyes looking at the flat horizontal surface. A pillow placed under knees or behind knees may be helpful.
 a. Sway back, pushing stomach downward. Tuck chin in and look at the flat horizontal surface (FIG. 11A).
 b. Hold for 10 seconds, then relax and return to starting position.
 c. Arch back, pushing back upward, and lower head toward the flat horizontal surface (FIG. 11B).
 d. Hold for 10 seconds.
 e. Maintain a rounded back, move body backward until buttocks rests on heels, stretching hands out in front of body (FIG. 11C).

f. Hold for 20 seconds, then relax and return to starting position.

g. Repeat two times for a total of three repetitions.

Figure 12A:
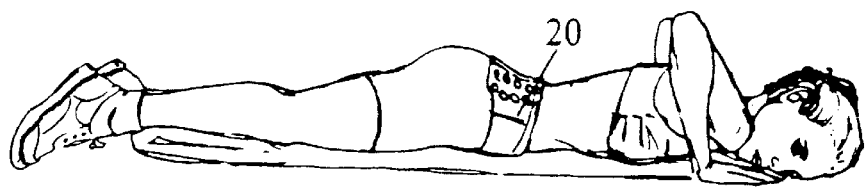
FIGS. 12A and 12B show a preferred procedure for performing the Extension (full press up) Exercise.
Figure 12B:
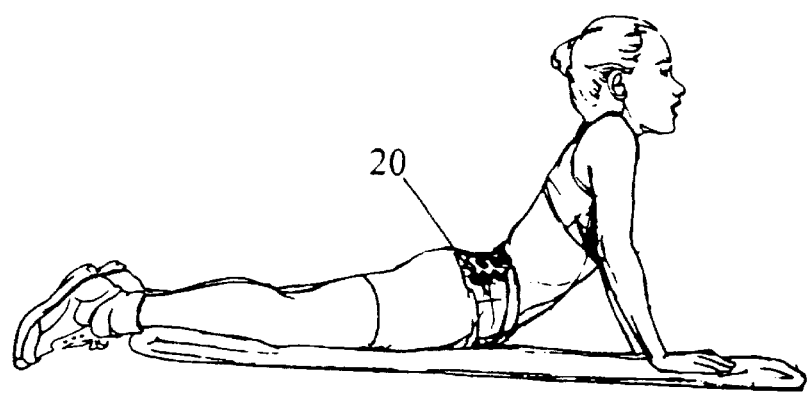

2. Full Press Extension (FIG. 12A–B)

Starting position: lying on stomach on a flat horizontal surface, arms at sides, head turned to the side.

a. Place hands palms down next to shoulders (FIG. 12A).

b. Push upper body up off the flat horizontal surface, straightening arms. Keep hips on the flat horizontal surface and eyes looking forward (FIG. 12B).

c. Hold for 10 seconds, then relax and return to starting position.

d. Repeat two times for a total of three repetitions.

Figure 12C:
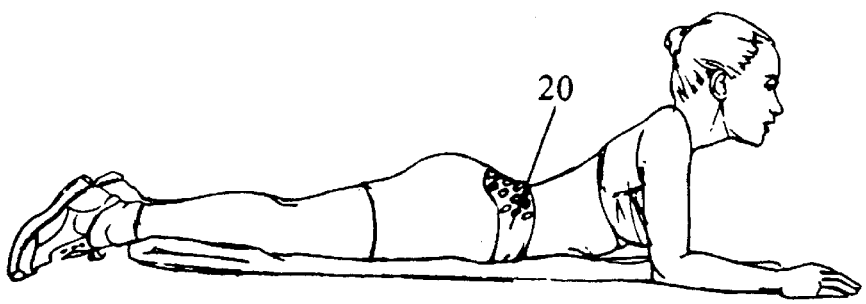
FIGS. 12C and 12D show two alternative positions for performing a preferred procedure for performing the Extension (partial press up) Exercise.
Figure 12D:
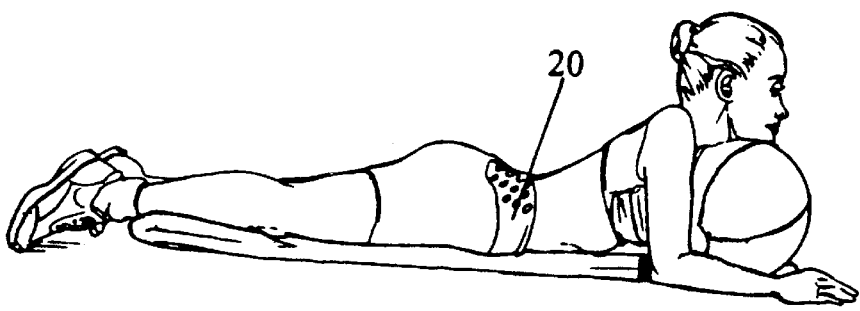

3. Partial Press Extension (FIG. 12C–D)

Starting position: lying on stomach on a flat horizontal surface, arms at sides, head turned to the side.

a. Place hands palms down next to shoulders.

b. Push upper body up off the flat horizontal surface to rest on forearms. Keep hips on the flat horizontal surface and eyes looking forward (FIG. 12C).

c. Hold for 20 seconds, then relax and return to starting position.

d. Repeat two times for a total of three repetitions.

In the alternative, hold an exercise ball between forearms for upper body support (FIG. 12D).

Figure 13:

4. Standing Extension (FIG. 13)

Starting position: standing tall, feet shoulder-width apart, chin tucked in.

a. Place palms on the small of back, fingers pointing down.

b. Keep head up, lean back slowly as far as possible.

c. Hold for 20 seconds, then relax and return to starting position.

d. Repeat two times for a total of three repetitions.

Figure 14:

5. Side Stretch (FIG. 14)

Starting position: standing tall, feet shoulder-width apart, hands at sides, chin tucked in.

a. Place left hand on left hip. Bend to the right, reaching downward with right hand toward the outside of right knee. Do not let upper body bend forward.

b. Hold for 10 seconds, then relax and return to starting position.

c. Repeat two times for a total of three repetitions.

d. Repeat steps a–b bending to the left with right hand on right hip.

e. Repeat two times for a total of three repetitions

6. Hip Stretch (FIG. 15)

Figure 15A:
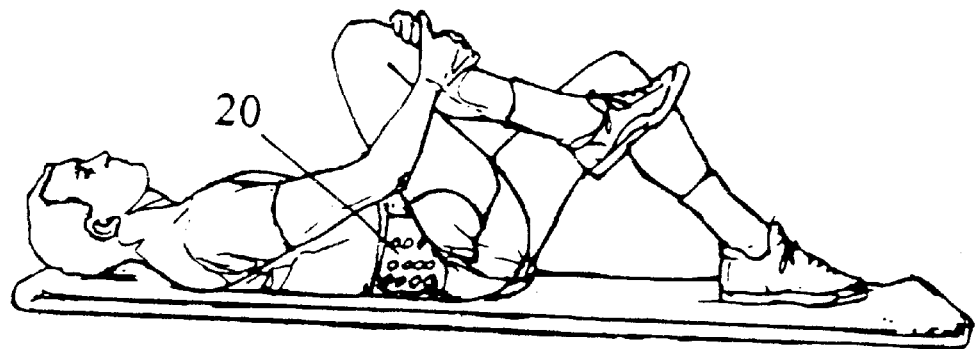
FIG. 15A shows a preferred procedure for performing the Hip Stretch Exercise.

Starting position: lying on back, knees bent, feet on a flat horizontal surface, arms at sides.

a. With both hands, pull right knee toward chest. Keep left knee bent with left foot on the flat horizontal surface (FIG. 15A).

b. Hold for 20 seconds, then relax and return to starting position.

c. Repeat two times for a total of three repetitions.

d. Repeat steps a–b pulling left knee toward chest.

e. Repeat two times for a total of three repetitions.

f. With both hands, pull both knees toward chest.

g. Hold for 20 seconds, then relax and return to starting position.

h. Repeat two times for a total of three repetitions.

Figure 15B:
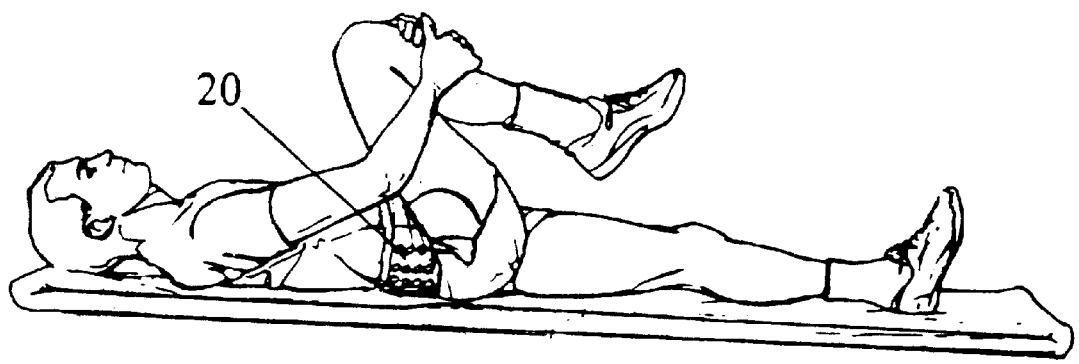
FIG. 15B shows an alternative position for performing a preferred procedure for performing the Hip Stretch Exercise.

In the alternative, straighten the knee of the leg on the flat horizontal surface to intensify the stretch (FIG. 15B).

7. Hamstring Stretch (FIG. 16)

Figure 16A:
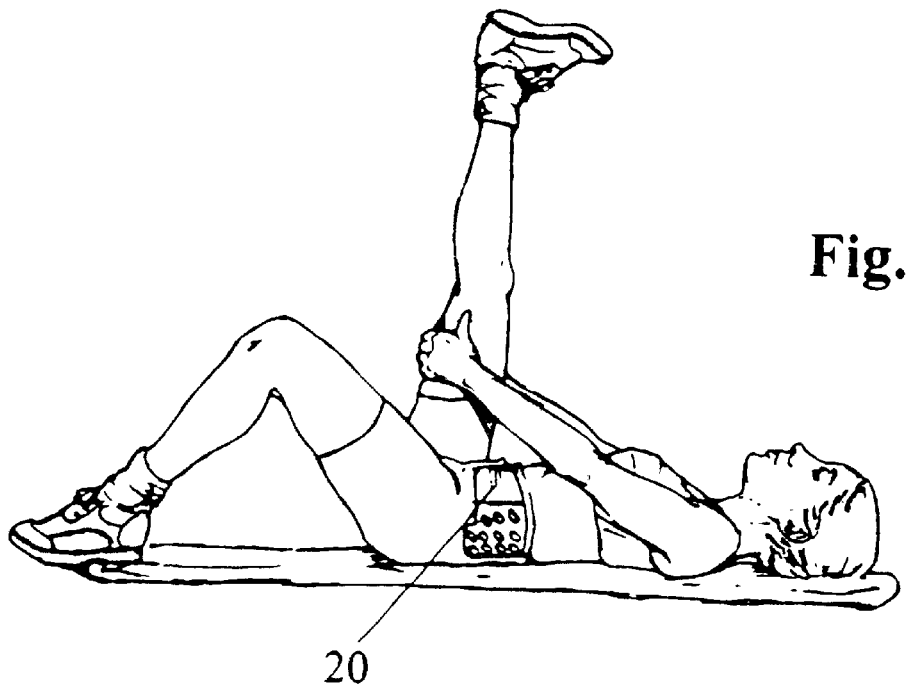
FIG. 16A shows a preferred procedure for performing the Hamstring Stretch Exercise.

Starting position: lying on back, knees bent with feet on a flat horizontal surface, arms at sides.

a. With both hands, pull right knee toward chest. Keep left knee bent and left foot on the flat horizontal surface.

b. Extend right leg to straighten right knee. Grasp the back of right thigh with both hands and flex ankle such that toes point toward body (FIG. 16A).

c. Hold for 20 seconds, then relax and return to starting position.

d. Repeat steps a–c with left leg.

e. Repeat two times for a total of three repetitions.

Figure 16B:
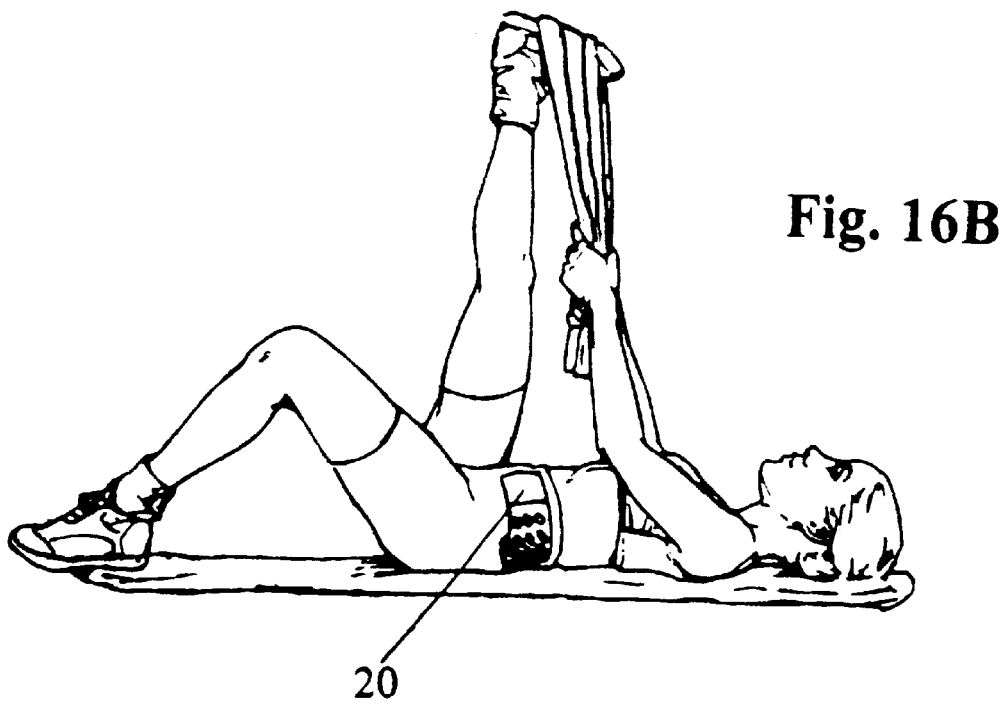
FIG. 16B shows an alternative position for performing a preferred procedure for performing the Hamstring Stretch Exercise.

In the alternative, straighten the knee of the leg with foot on the flat horizontal surface during the stretch or wrap a towel around upright foot and pull down slightly (FIG. 16B).

8. Lower Trunk Rotation FIG. 17)

Figure 17A:
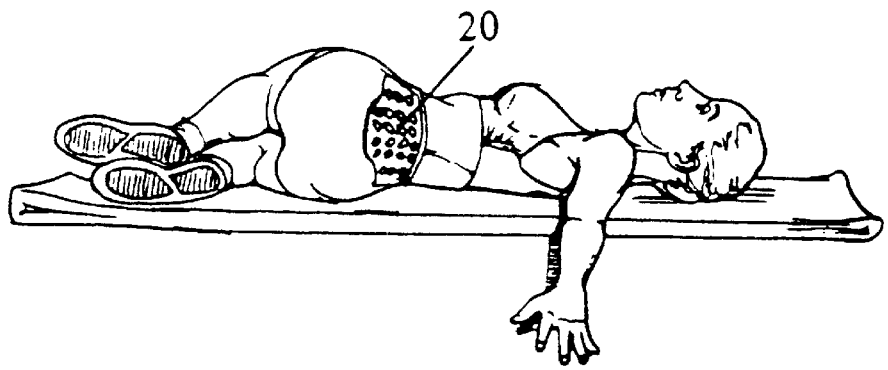
FIGS. 17A and 17B show a preferred procedure for performing the Lower Trunk Rotation Exercise.
Figure 17B:
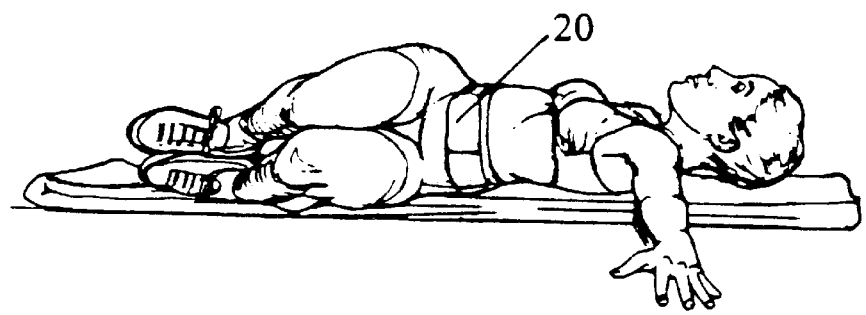

Starting position: lying on back, knees bent, feet on a flat horizontal surface, arms at sides.

a. Slowly roll knees to the right as close to the flat horizontal surface as possible. Keep shoulders on the flat horizontal surface (FIG. 17A).

b. Hold for 20 seconds.

c. Slowly roll knees to the left as close to the flat horizontal surface as possible. Keep shoulders on the flat horizontal surface (FIG. 17B).

c. Hold for 20 seconds, then relax and return to starting position.

d. Repeat two times for a total of three repetitions.

Figure 17C:
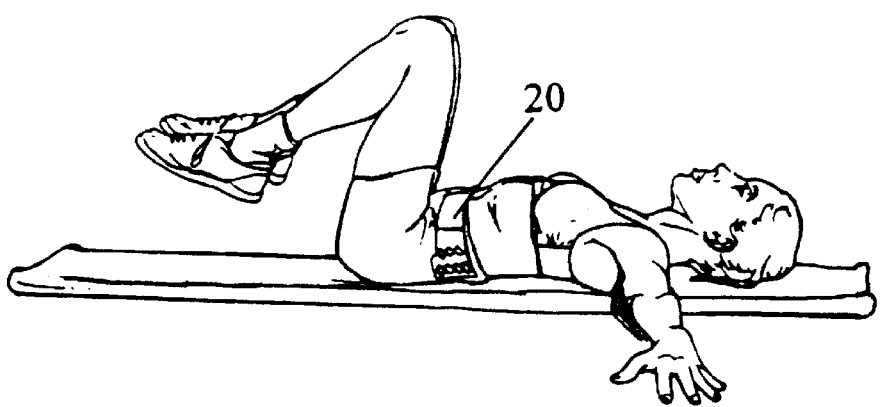
FIG. 17C shows an alternative position for performing a preferred procedure for performing the Lower Trunk Rotation Exercise.

In the alternative, bring both knees up toward chest, lifting feet off the flat horizontal surface. Slowly roll both knees to the right and then to the left. Make sure back stays flat with shoulders on a flat horizontal surface (FIG. 17C).

9. Pelvic Tilt (FIG. 18)

Figure 18A:
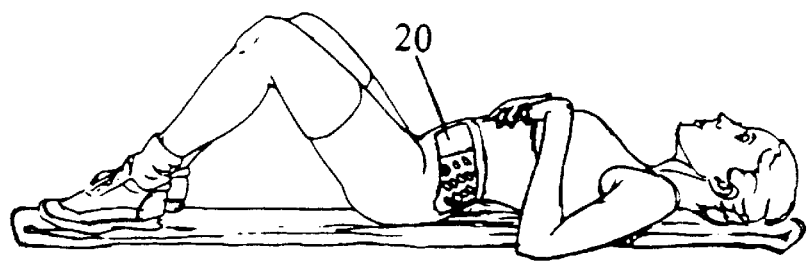
FIGS. 18A and 18B show a preferred procedure for performing the Pelvic Tilt Exercise.
Figure 18B:
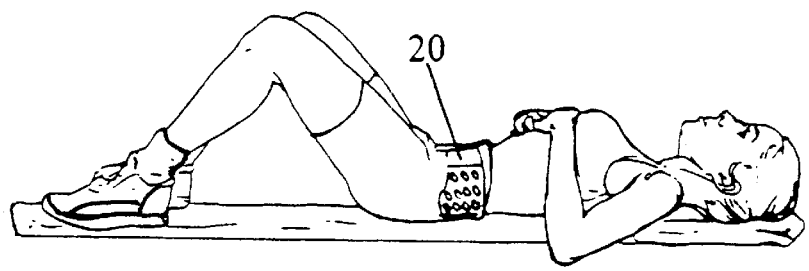

Starting position: lying on back on a flat horizontal surface, knees bent, feet on the flat horizontal surface.

a. Arch the lower back and push stomach upward (FIG. 18A).

b. Flatten lower back against the flat horizontal surface by tightening the muscles of the abdomen and buttock (FIG. 18B).

c. Hold for 20 seconds, then relax and return to starting position.

c. Repeat two times for a total of three repetitions.

Figure 18C:
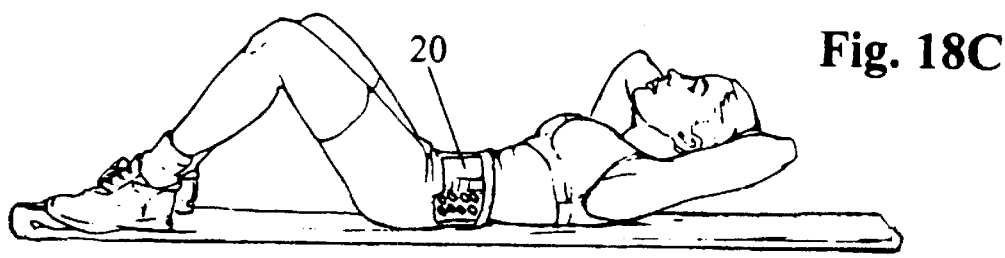
FIG. 18C shows an alternative position for performing a preferred procedure for performing the Pelvic Tilt Exercise.

In the alternative, place both hands behind head and partially curl upper body in toward knees during step b (FIG. 18C).

10. Lower Abdominal Strengthening (FIG. 19)

Figure 19A:
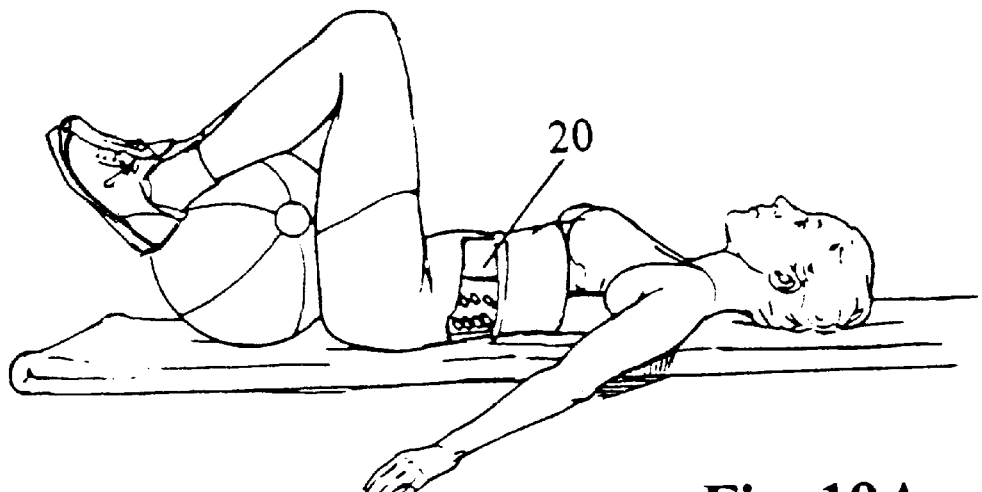
FIGS. 19A and 19B show a preferred procedure for performing the Lower Abdominal Strengthening Exercise.
Figure 19B:
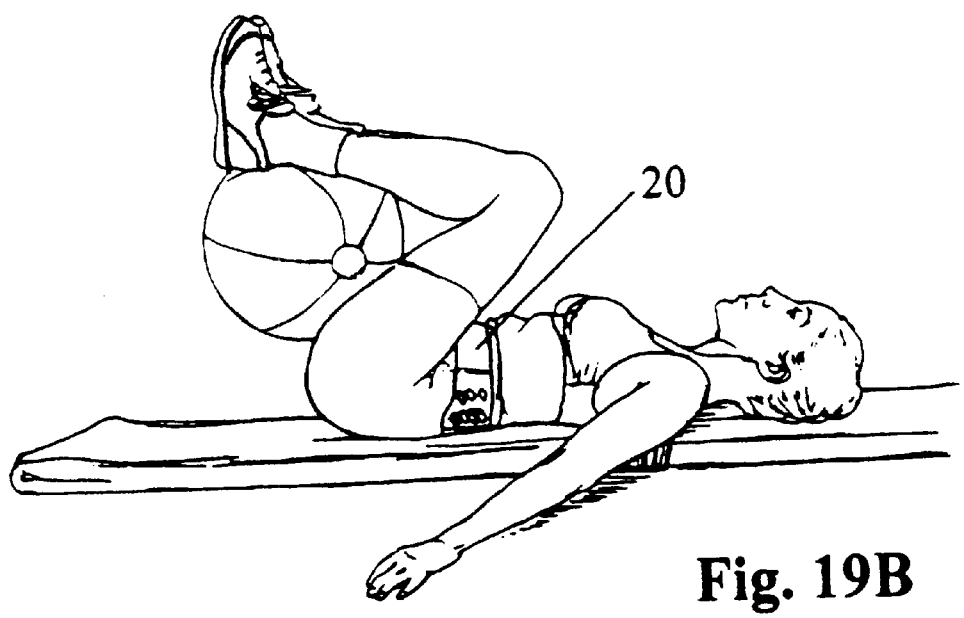
Figure 20:
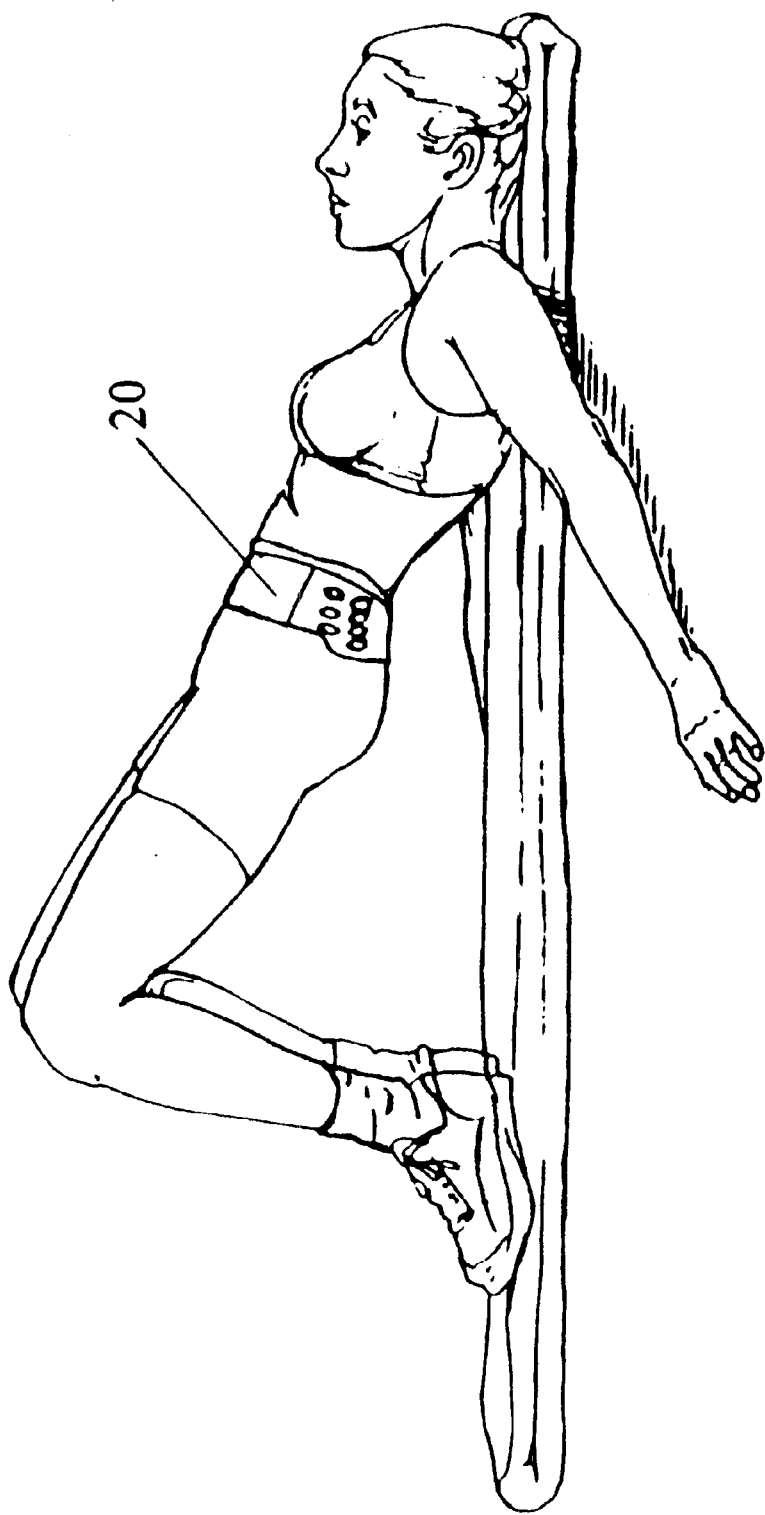

Starting position: lying on back, knees bent.

a. Place an exercise ball between heels and buttock (FIG. 19A).

b. Flatten lower back against a flat horizontal surface by tightening the muscles of abdomen and buttock. Slowly bring both knees toward chest and then back down to the flat horizontal surface. Do not arch back (FIG. 19B).

c. Repeat two times for a total of three repetitions.

11. Lower Abdominal Strengthening—"The Bridge" position (FIG. 20) Starting position: lying on back on a flat horizontal surface, knees bent, feet and elbows on the flat horizontal surface.

a. Flatten lower back against the flat horizontal surface by tightening the muscles of abdomen and buttock.

b. Lift hips and lower back upward to form a straight line from knees to chest.

c. Hold for 20 seconds, then relax and return to starting position.

d. Repeat two times for a total of three repetitions.

III. Exercises for Knee Pain

The following exercises, shown in FIGS. 21–28, promote muscular strength, endurance, flexibility, and increase tissue healing and rehabilitation to a human in need of relief from acute, recurrent, and/or chronic pain, including homotopic, heterotopic, muscular, and/or skeletal pain, due to, but not limited to, injury and/or inflammation of the user's knee. All of the following exercises are to be performed according the Methods of Treating Pain, described below. That is, the user is instructed to apply topical heat, i.e., from about 32° C. to about 50° C., to the afflicted area of the body from about thirty minutes to about six hours prior to beginning the therapeutic exercise or set of exercises, to completion to about six hours after completion of the therapeutic exercise or set of exercises. Preferably the user performs the following exercises while wearing a thermal knee wrap 30, preferably the ThermaCare® HeatWrap for the knee.

A. Knee/Leg Flexibility Exercises

1. Standing Quadriceps Stretch (FIG. 21)

Starting position: standing comfortably upright facing a vertical surface or chair for support.

a. Bend right knee to stand on left leg, using the vertical surface or chair for support. Slightly bend left knee.

b. Grasp right ankle with right hand behind body.

c. Slowly bring heel in toward buttock, keeping knees aligned and stomach pulled in. Do not arch back during the stretch (FIG. 21A).

d. Hold for 20 seconds, then relax and return to starting position.

e. Repeat steps a–d standing on right leg, grasping left ankle.

f. Repeat steps a–e two times for a total of three repetitions.

Figure 21B:
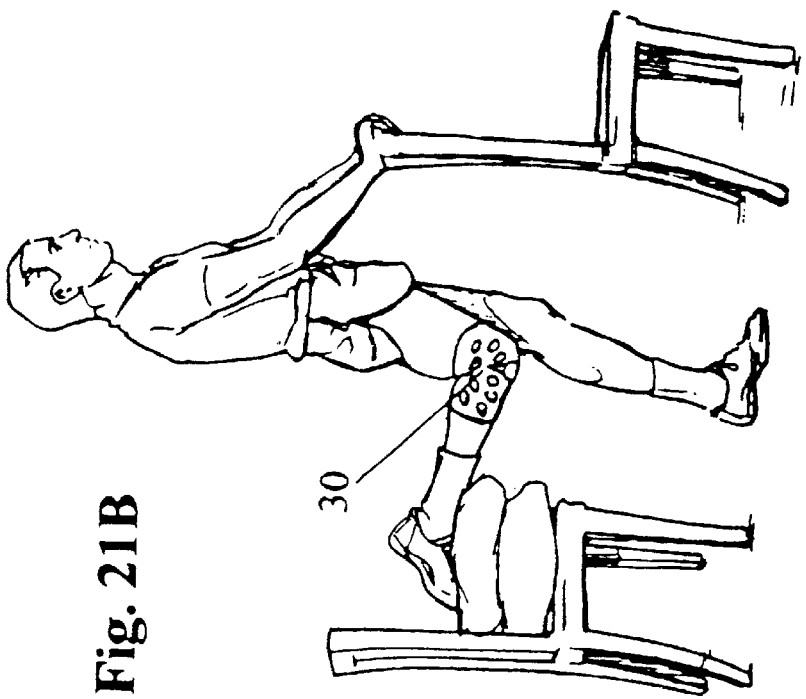
FIGS. 21A and 21B show a preferred procedure for performing the Quadriceps Stretch Exercise.
Figure 21A:
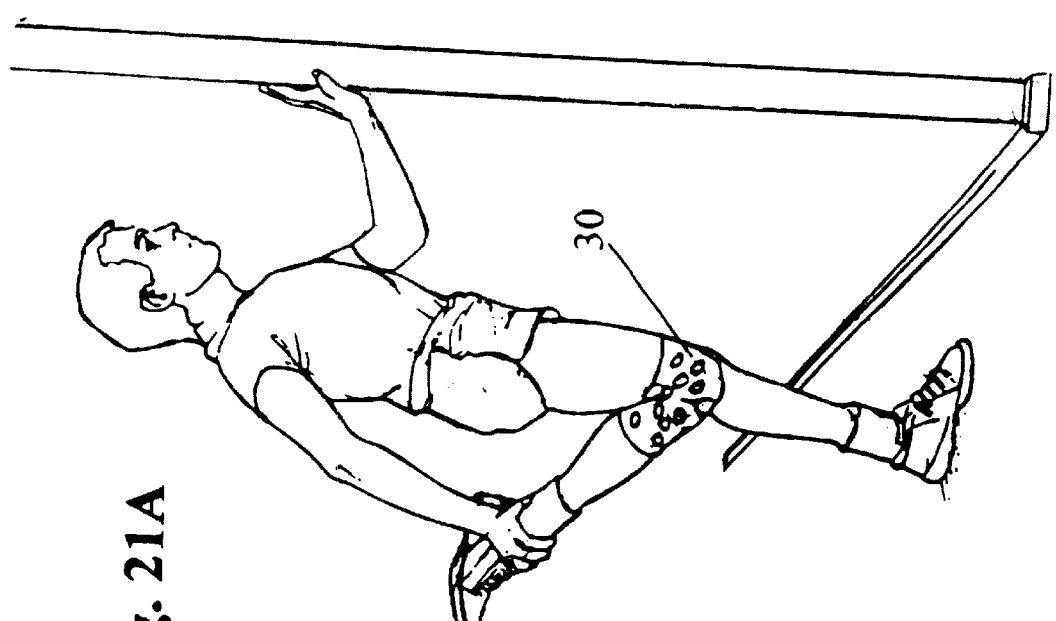

In the alternative, a chair and pillows may be used to support the foot of the leg being exercised (FIG. 21B).

Figure 22:
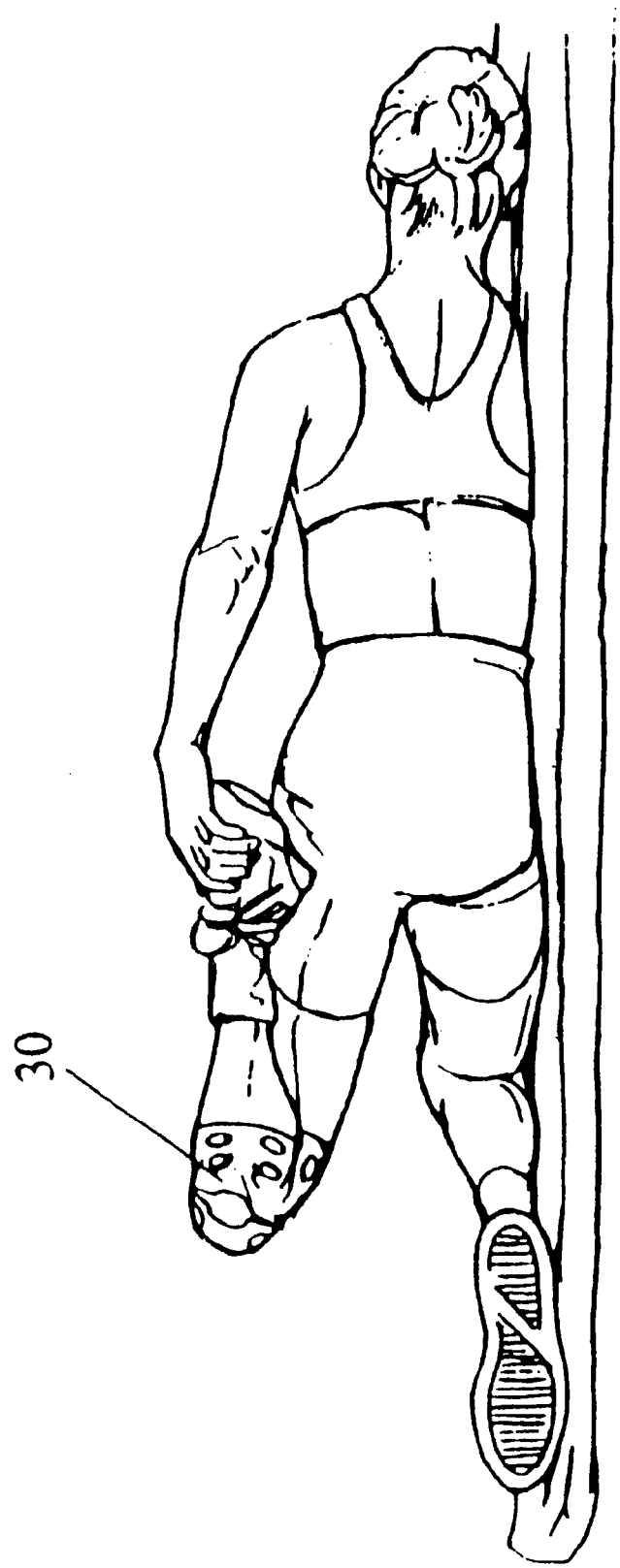

2. Reclining Quadriceps Stretch (FIG. 22)

Starting position: lying on right side on a flat horizontal surface, knees bent.

a. Grasp left ankle with left hand behind body.

b. Slowly bring heel in toward buttock. Keep stomach pulled in and do not arch back.

c. Hold for 20 seconds, then relax and return to starting position.

d. Repeat steps a–c lying on left side, grasping right ankle.

e. Repeat steps a–d two times for a total of three repetitions.

3. Calf Muscle stretch (FIG. 23)

Figure 23B:
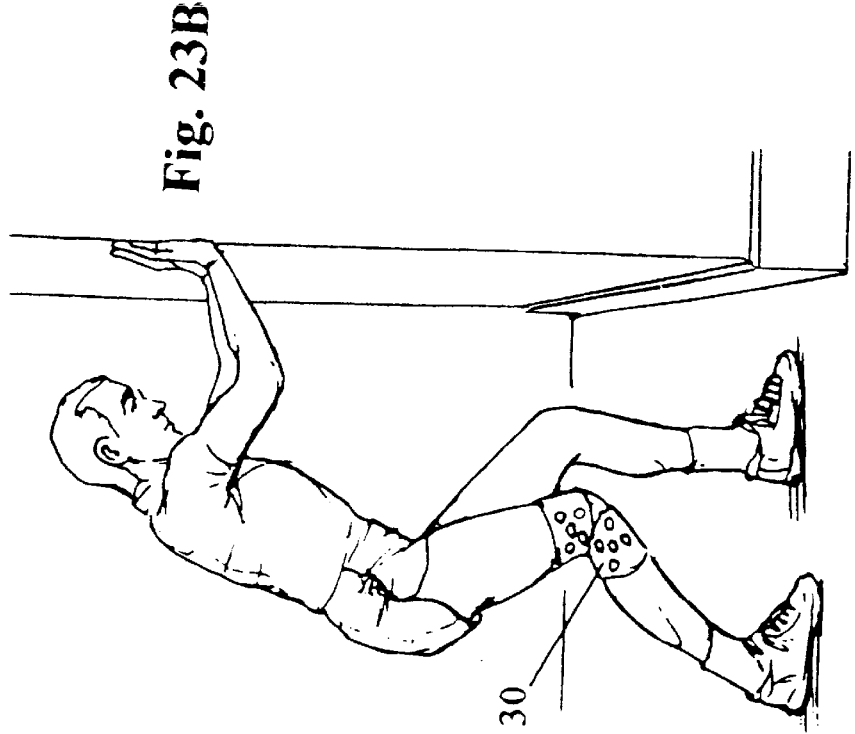
FIGS. 23A and 23B show a preferred procedure for performing the Calf Muscle Stretch Exercise.
Figure 23A:
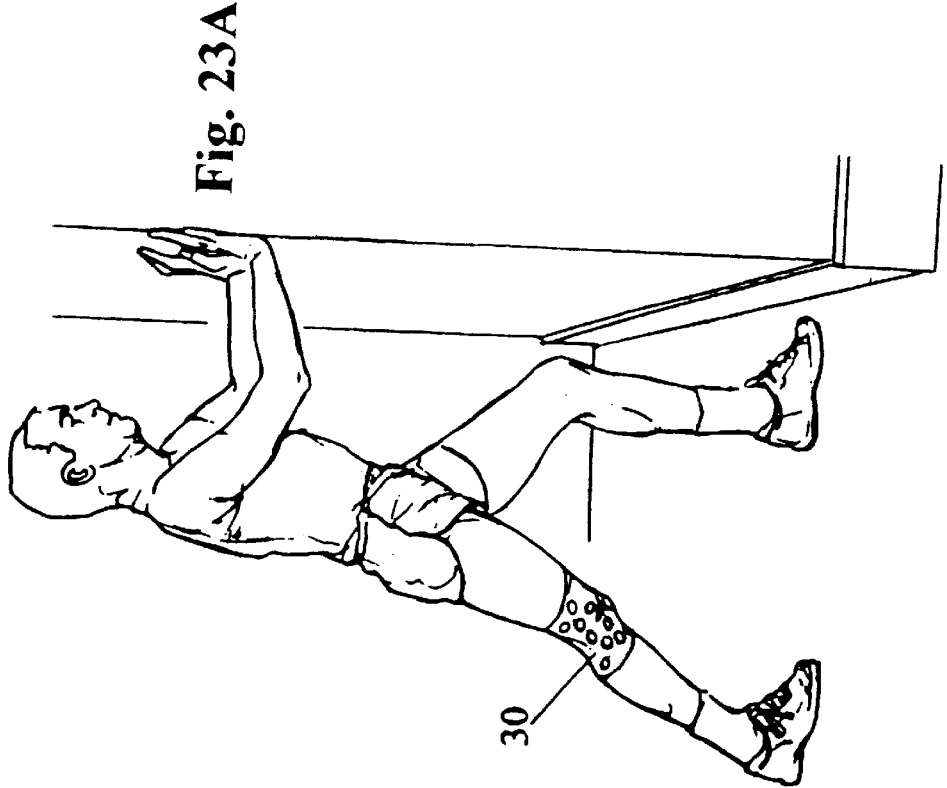

Starting position: standing on a flat horizontal surface facing a vertical surface, both hands against the vertical surface, feet shoulder-width apart and perpendicular to the vertical surface.

a. Step back with right foot, keeping right heel flat on the flat horizontal surface and right foot and knee straight. Bend left knee and lean into the vertical surface (FIG. 23A).

b. Hold for 20 seconds.

c. Bend right knee, keeping right heel flat on the flat horizontal surface, shifting weight to right foot while moving down into a squat position (FIG. 23B).

d. Hold for 20 seconds, then relax and return to starting position.

e. Repeat steps a–d stepping back with the left foot.

f. Repeat steps a–e two times for a total of three repetitions.

4. Reclining Hamstring Stretch (FIG. 24)

Figure 24A:
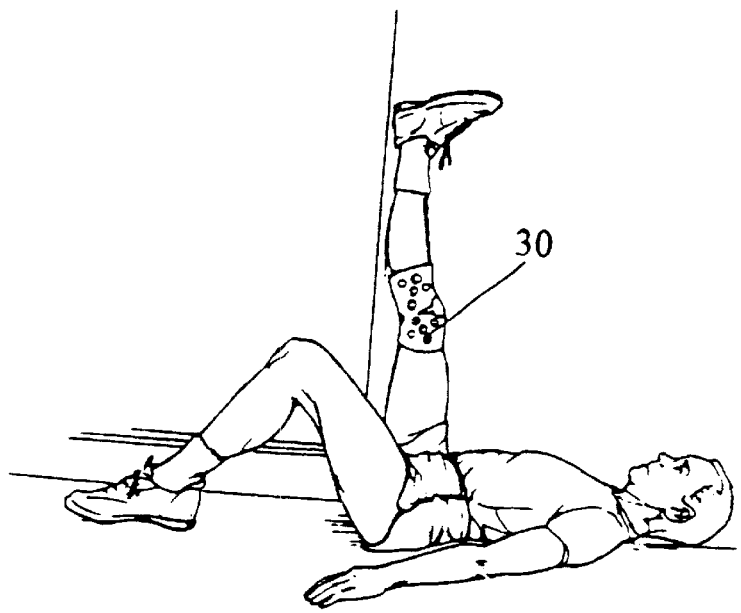
FIGS. 24A and 24B show a preferred procedure for performing the Hamstring Stretch Exercise.

Starting position: lying on back on a flat horizontal surface near a vertical surface for support.

a. Bend both knees, extend right leg and place the heel of right foot against the vertical surface.

b. Straighten right knee against the vertical surface. Keep left knee bent and left foot on the flat horizontal surface (FIG. 24A).

c. Hold for 20 seconds, then relax and return to starting position.

d. Repeat steps a–c two times for a total of three repetitions.

e. Repeat steps a–d with left foot against the vertical surface.

Figure 24B:
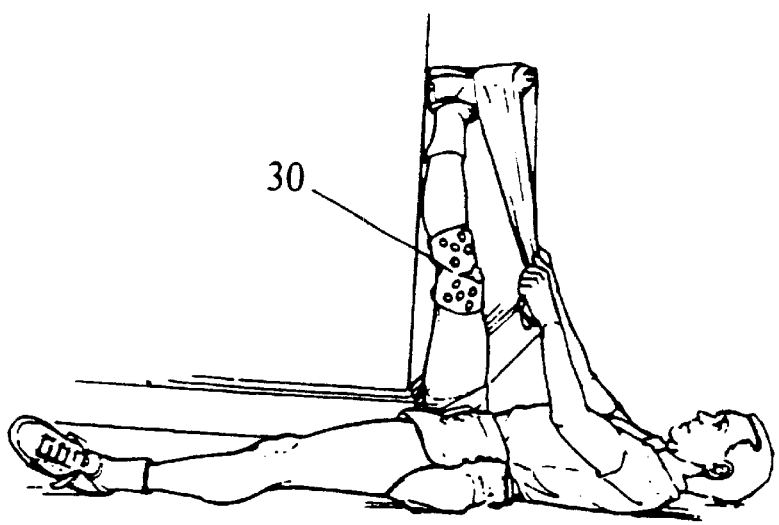

In the alternative, straighten knee of the foot on the flat horizontal surface and/or wrap a towel around the upright foot and pull down slightly (FIG. 24B).

Figure 25:
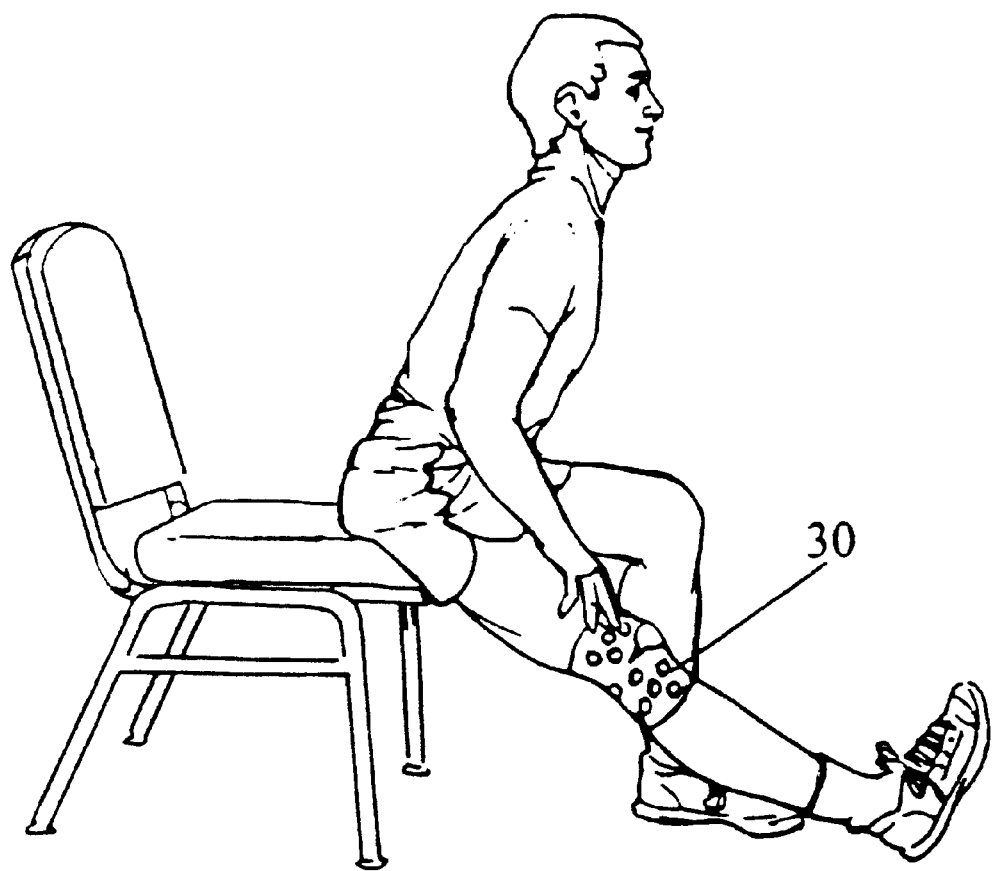

5. Sitting Hamstring Stretch (FIG. 25)

Starting position: sitting up tall on the edge of a elevated flat horizontal surface, knees bent, hands resting on thighs.

a. Straighten right knee. Keep right heel on a non-elevated flat horizontal surface, flex ankle (toes toward shin).

b. Keep back straight, while leaning forward from the waist (FIG. 25).

c. Hold for 20 seconds, then relax and return to starting position.

d. Repeat steps a–c with the left knee.

f. Repeat steps a–d two times for a total of three repetitions.

B. Knee/Leg Strengthening Exercises

1. Vertical Squat (FIG. 26)

Figure 26B:
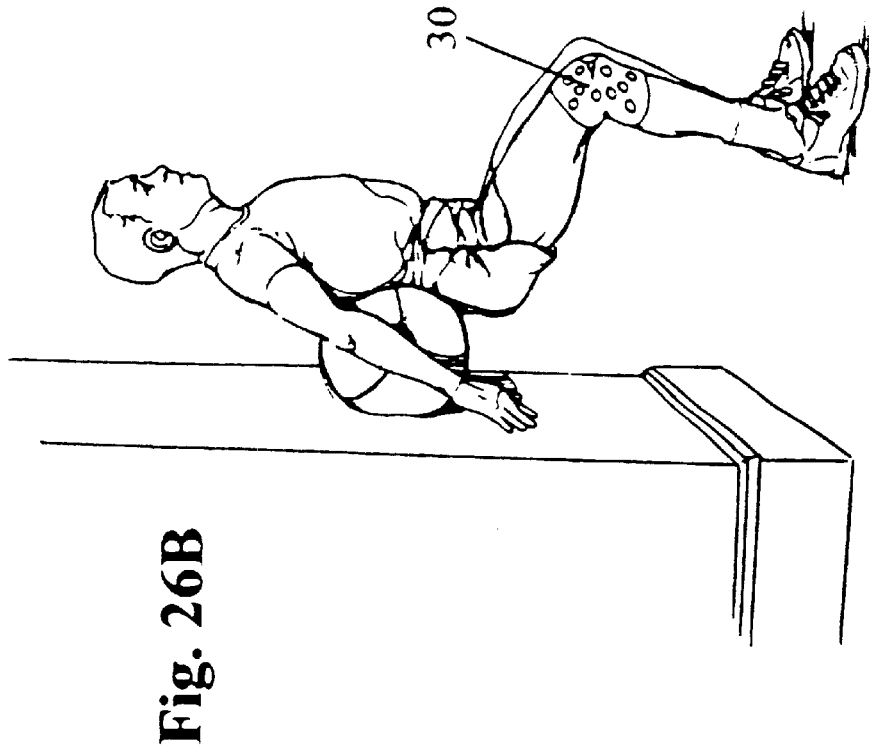
FIGS. 26A and 26B show a preferred procedure for performing the Vertical Squat Exercise.
Figure 26A:
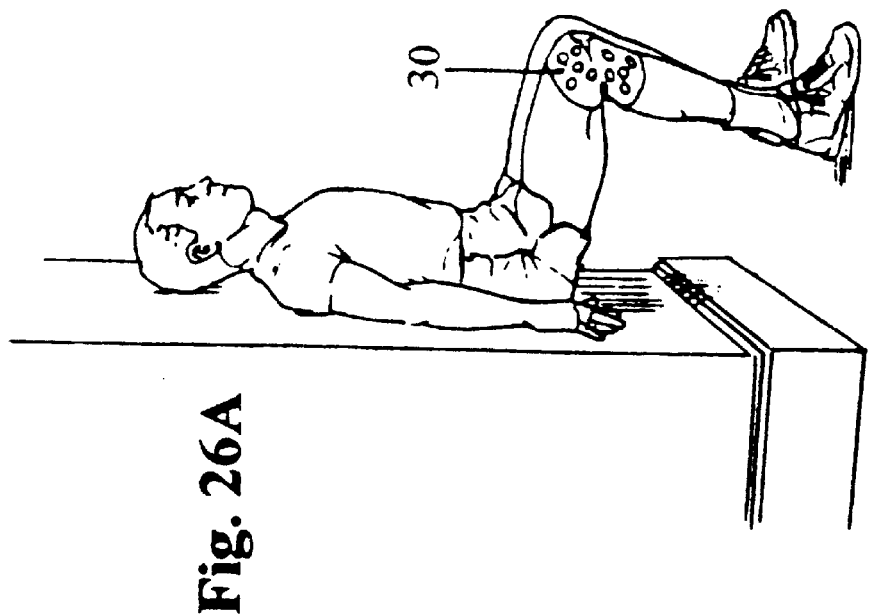

Starting position: leaning with back against a smooth vertical surface, feet straight and shoulder-width apart about 1.5 feet (30.5 cm) out from the vertical surface.

a. Slowly slide down the vertical surface to a sitting position, with head, shoulders, arms, back, hips, and palms of hands all pressing against the vertical surface. If needed, move feet further out to keep knees from jutting out over toes (FIG. 26A).

b. Hold for 20 seconds, then relax and return to starting position.

c. Repeat steps a–b two times for a total of three repetitions.

Figure 26D:
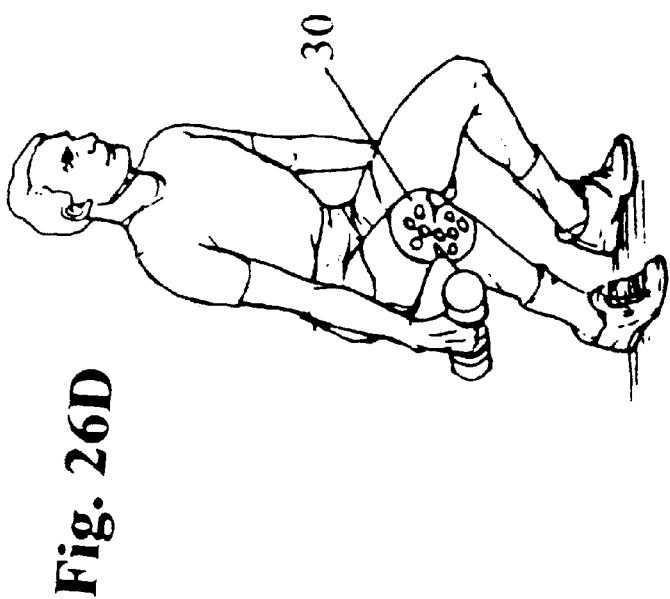
FIGS. 26C and 26D show two alternative positions for performing a preferred procedure for performing the Vertical Squat Exercise.
Figure 26C:
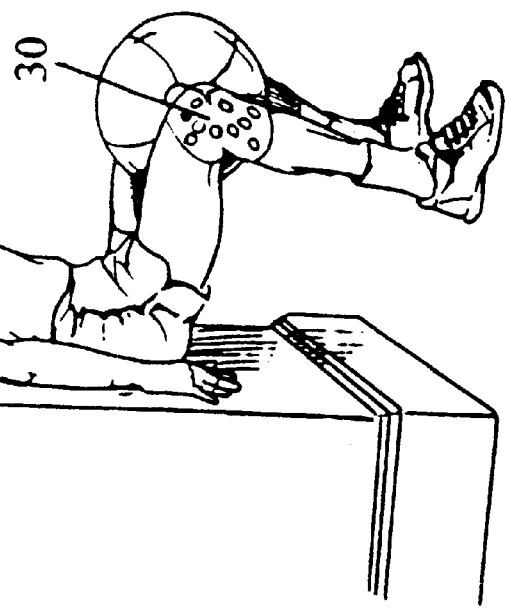

In the alternative, an exercise ball may be held between back and the vertical surface (FIG. 26B), between knees (FIG. 26C), or the exercise may be performed holding weights without leaning against the vertical surface (FIG. 26D).

Figure 27:
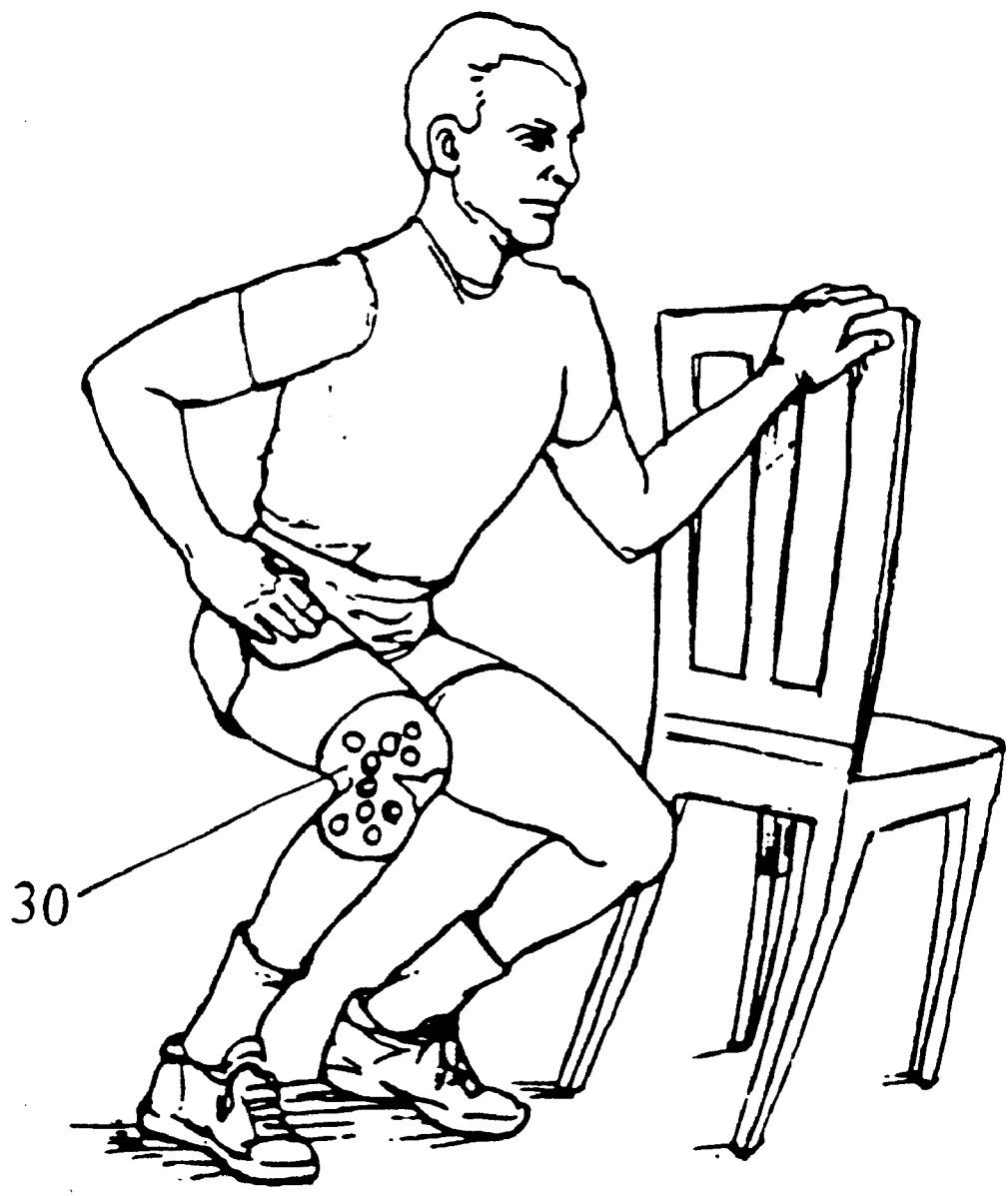

2. Standing Squat (FIG. 27)

Starting position: standing with side to the back of a chair for support, feet straight and shoulder-width apart.

a. Hold the back of the chair with hand.

b. Slowly lower body into a squat position.

c. Hold for 20 seconds, then relax and return to starting position.

d. Repeat steps a–c two times for a total of three repetitions.

Figure 28:
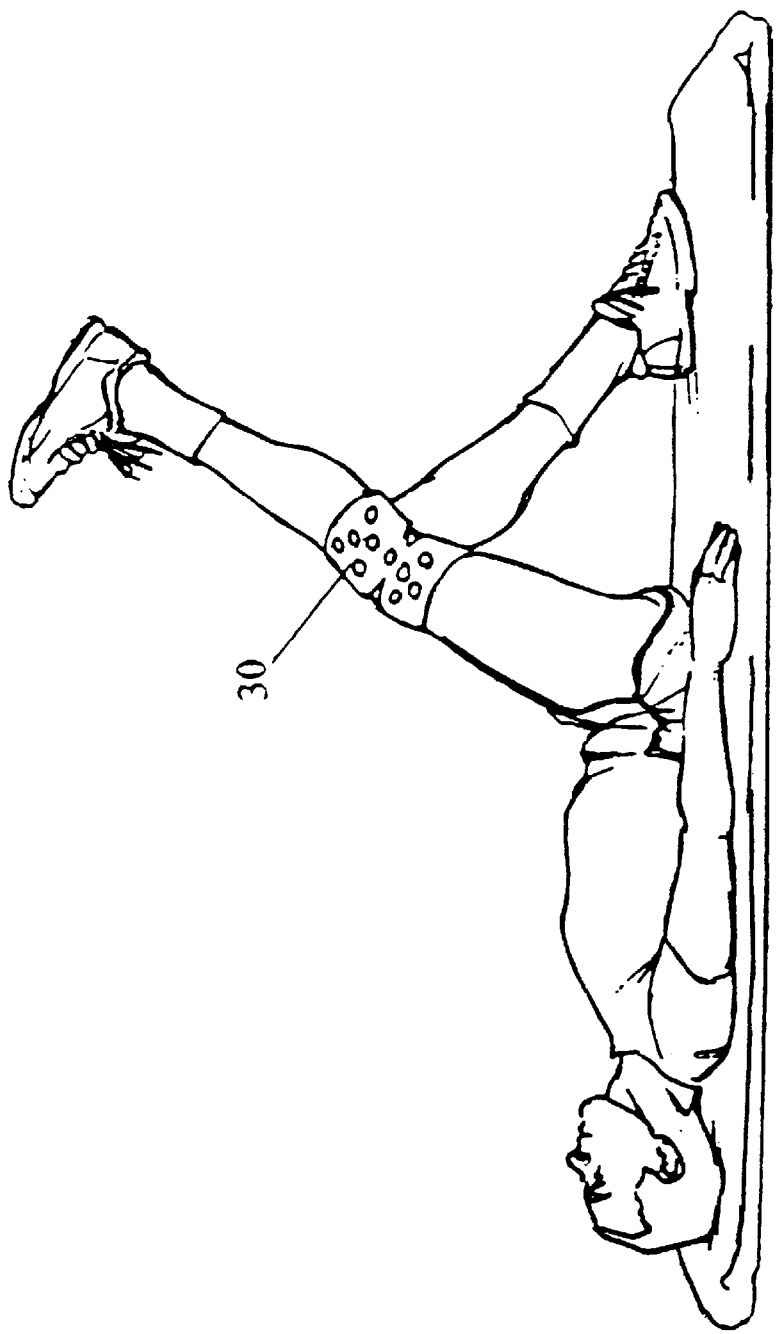

3. Leg Lift (FIG. 28)

Starting position: lying on back on a flat horizontal surface, arms at sides, legs straight.

a. Bend left knee with left foot flat on the horizontal surface.

b. Keeping right knee straight and back flat, flex ankle (toes toward shin) and slowly lift right leg up to the level of left knee, thighs and knees should be aligned.

c. Lower right leg slowly but do not relax.

d. Repeat steps b 14 times without stopping, keeping right leg straight, for a total of 15 repetitions.

e. Relax and return to starting position.

f. Bend right knee with right foot flat on the horizontal surface.

g. Keeping left knee straight and back flat, flex ankle (toes toward shin) and slowly lift left leg up to the level of right knee, thighs and knees should be aligned.

h. Repeat step g 14 times without stopping, keeping left leg straight, for a total of 15 repetitions.

In the alternative, wrap a weight around the ankle of the working leg.

IV. Exercises for Abdominal Pain

The following exercises, shown in FIGS. 29–34, promote muscular strength, endurance, flexibility, and increase tissue healing and rehabilitation to a human in need of relief from acute, recurrent, and/or chronic pain, including homotopic, heterotopic, muscular, and/or skeletal pain, due to, but not limited to, injury and/or inflammation of the user's abdomen, such as dysmenorrhea. All of the following exercises are to be performed according the Methods of Treating Pain, described below. That is, the user is instructed to apply topical heat, i.e., from about 32° C. to about 50° C., to the afflicted area of the body from about thirty minutes to about six hours prior to beginning the therapeutic exercise or set of exercises, to completion to about six hours after completion of the therapeutic exercise or set of exercises. Preferably the user performs the following exercises while wearing a thermal body/abdominal wrap/patch 40, preferably the ThermaCare® HeatWrap for menstrual pain.

A. Abdominal Stretching Exercises

1. Cat Stretch (FIG. 29)

Figure 29A:
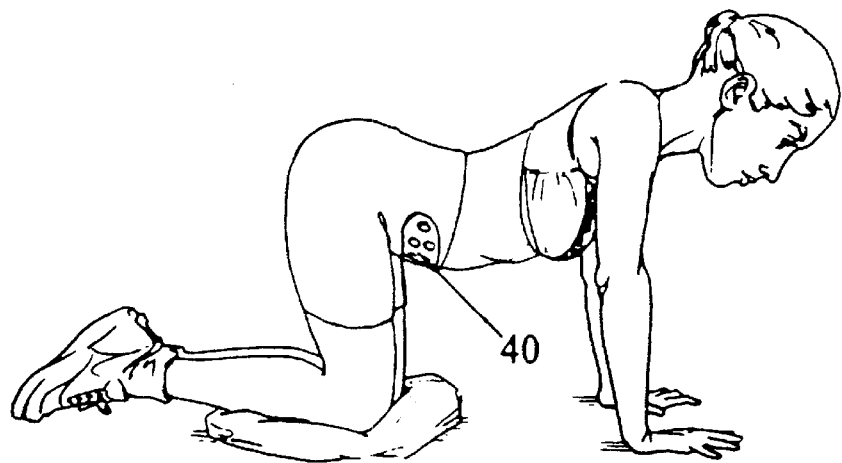
FIGS. 29A, 29B, and 29C show a preferred procedure for performing the Cat Stretch Exercise.
Figure 29B:
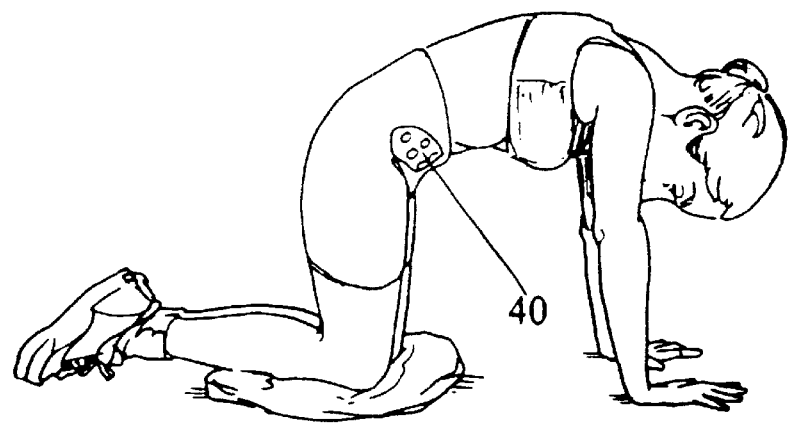
Figure 29C:
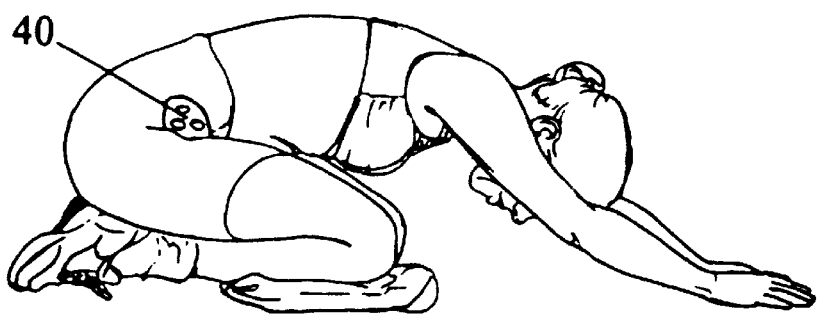

Starting position: on hands and knees on a flat horizontal surface, hands under shoulders, knees under hips, feet relaxed, looking straight ahead.

a. Sway back, pushing stomach toward the flat horizontal surface. Tuck chin in and look forward (FIG. 29A).

b. Hold for 10 seconds, then relax.

c. Arch back, pushing back upward, and drop head down (FIG. 29B).

d. Hold for 10 seconds. Maintain a arched back while performing step e.

e. Sit back on heels, stretching arms out in front and resting forehead on the flat horizontal surface (FIG. 29C).

f. Hold for 20 seconds, then relax and return to starting position.

g. Repeat steps a–f two times for a total of three repetitions.

2. Lower Trunk Rotation (FIG. 30)

Figure 30A:
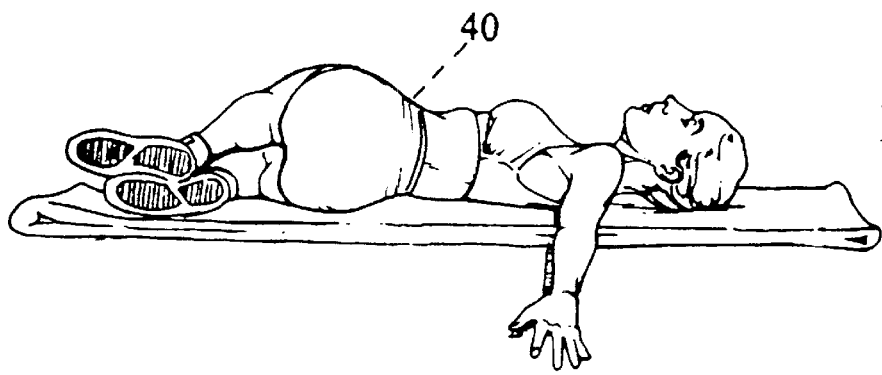
FIGS. 30A and 30B show a preferred procedure for performing the Lower Trunk Rotation Exercise.
Figure 30B:
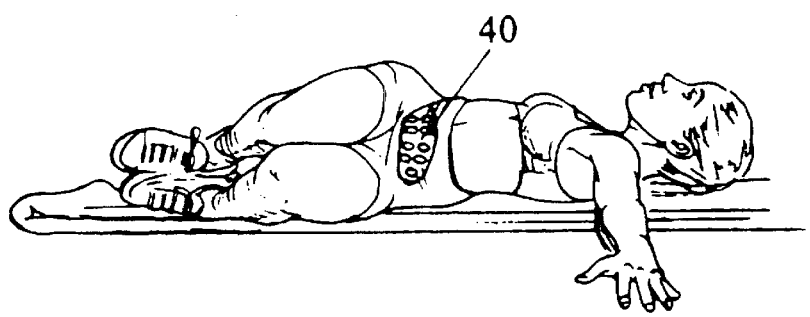

Starting position: lying on back, knees bent, feet on a flat horizontal surface, arms at sides.

a. Slowly roll knees to the right close to the flat horizontal surface. Keep shoulders on the flat horizontal surface (FIG. 30A).

b. Hold for 20 seconds, then slowly roll to the left side (FIG. 30B).

c. Hold for 20 seconds, then return to starting position.

d. Repeat steps a–c two times for a total of three repetitions.

Figure 30C:
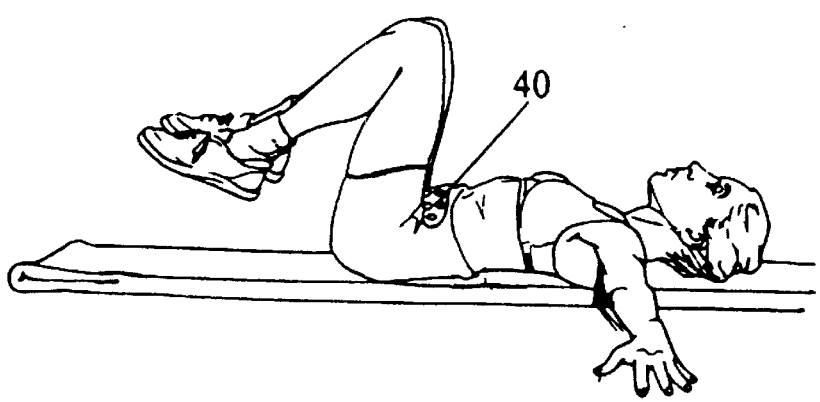
FIG. 30C shows an alternative position for performing a preferred procedure for performing the Lower Trunk Rotation Exercise.

In the alternative, bring both knees up toward chest, lifting feet off the flat horizontal surface (FIG. 30C). Repeat steps a–d for a total of three repetitions.

Figure 31:
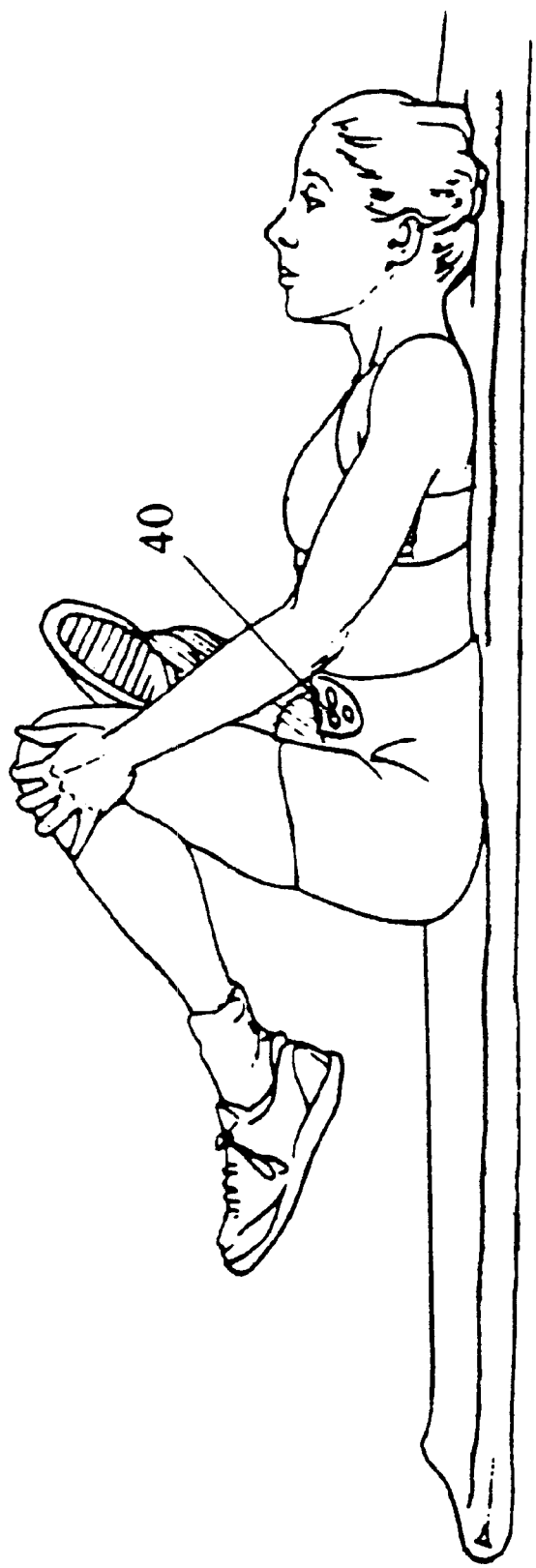

3. Buttock/Hip Stretch (FIG. 31)

Starting position: lying on back on a flat horizontal surface, knees bent a. Place the outside of right ankle against left thigh just above the knee.

b. Grasp the left leg just below knee and pull toward chest.

c. Hold for 20 seconds, then relax and return to starting position.

d. Place the outside of left ankle against right thigh just above the knee.

e. Grasp the right leg just below knee and pull toward chest.

f. Hold for 20 seconds, then relax and return to starting position.

g. Repeat steps a–f two times for a total of three repetitions.

4. Pelvic Tilt (FIG. 32)

Figure 32A:
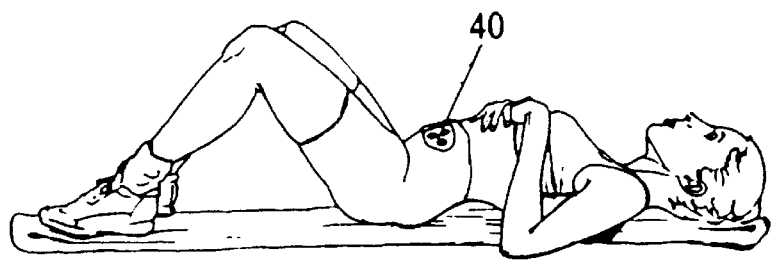
FIGS. 32A and 32B show a preferred procedure for performing the Pelvic Tilt Exercise.
Figure 32B:
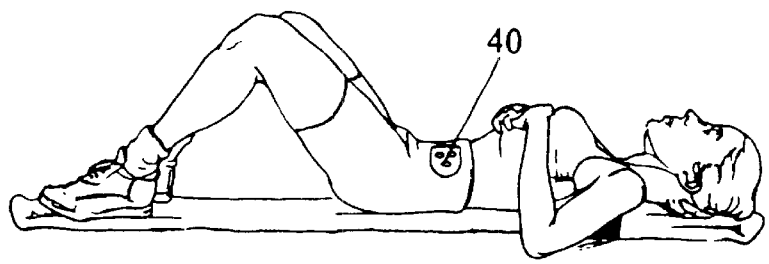

Starting position: lying on back on a flat horizontal surface, knees bent feet on the flat horizontal surface a. Arch the small of back up off the flat horizontal surface and push stomach upward (FIG. 32A). Hold for 20 seconds.

b. Flatten lower back against the flat horizontal surface by tightening the muscles of abdomen and buttock (FIG. 32B). Hold for 20 seconds.

c. Repeat steps a–b two times for a total of three repetitions.

Figure 32C:
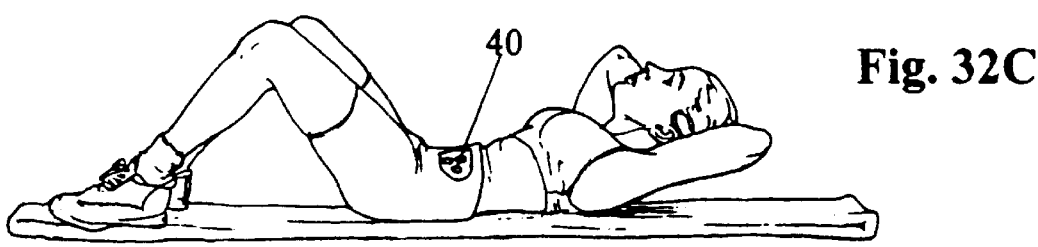
FIG. 32C shows an alternative position for performing a preferred procedure for performing the Pelvic Tilt Exercise.

In the alternative, place hands behind head and partially curl upper body in toward knees during step b (FIG. 32C).

5. Lower Abdominal Strengthening (FIG. 33)

Figure 33A:
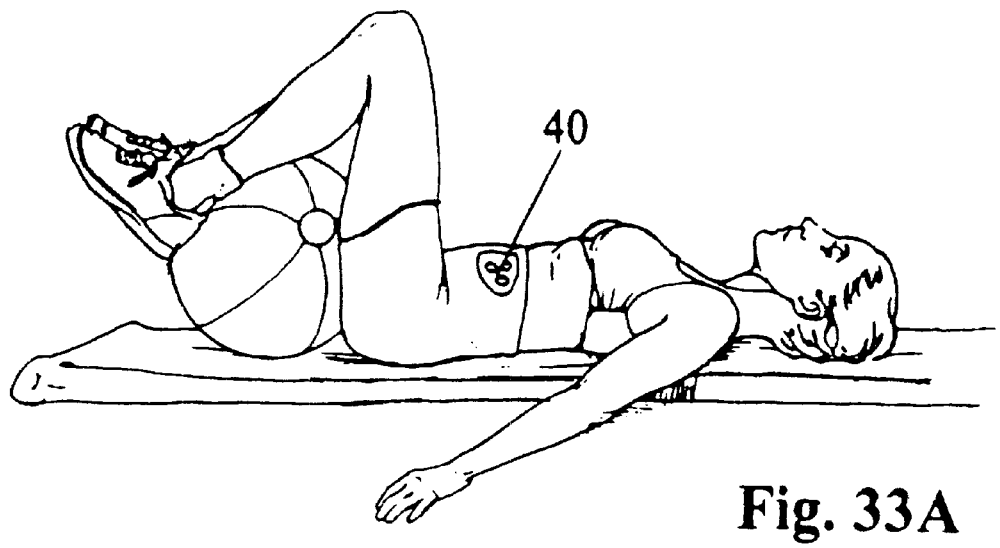
FIGS. 33A and 33B show a preferred procedure for performing the Lower Abdominal Strengthening Exercise.
Figure 33B:
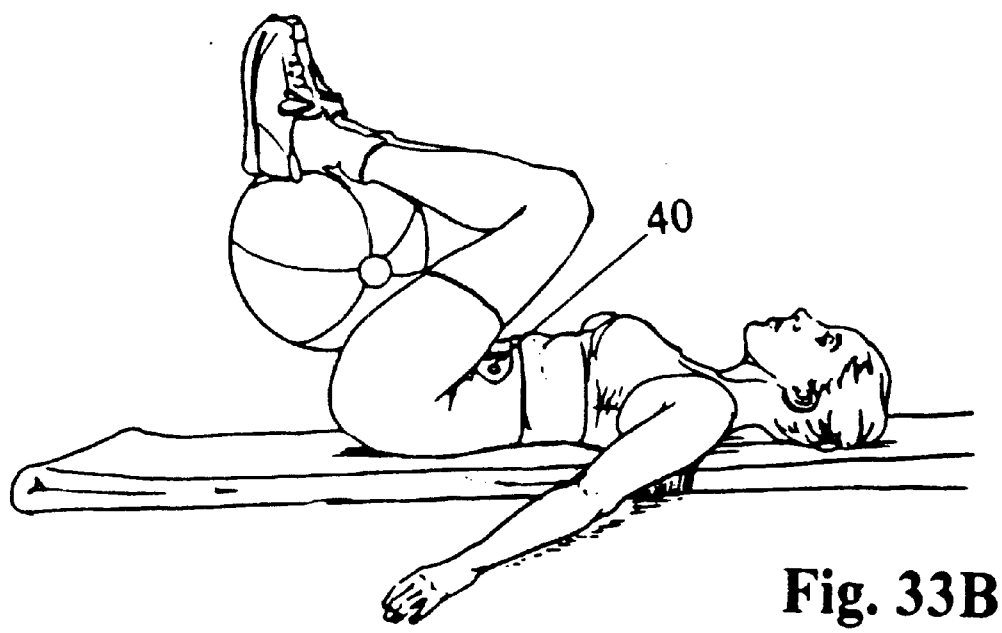

Starting position: lying on back on a flat horizontal surface, knees bent.

a. Place an exercise ball between heels and buttock (FIG. 33A).

b. Flatten lower back against the flat horizontal surface by tightening the muscles of abdomen and buttock. Slowly bring both knees up toward chest and then back down to the flat horizontal surface (FIG. 33B). Do not arch back.

c. Repeat steps a–b 14 times for a total of 15 repetitions.

Figure 34:
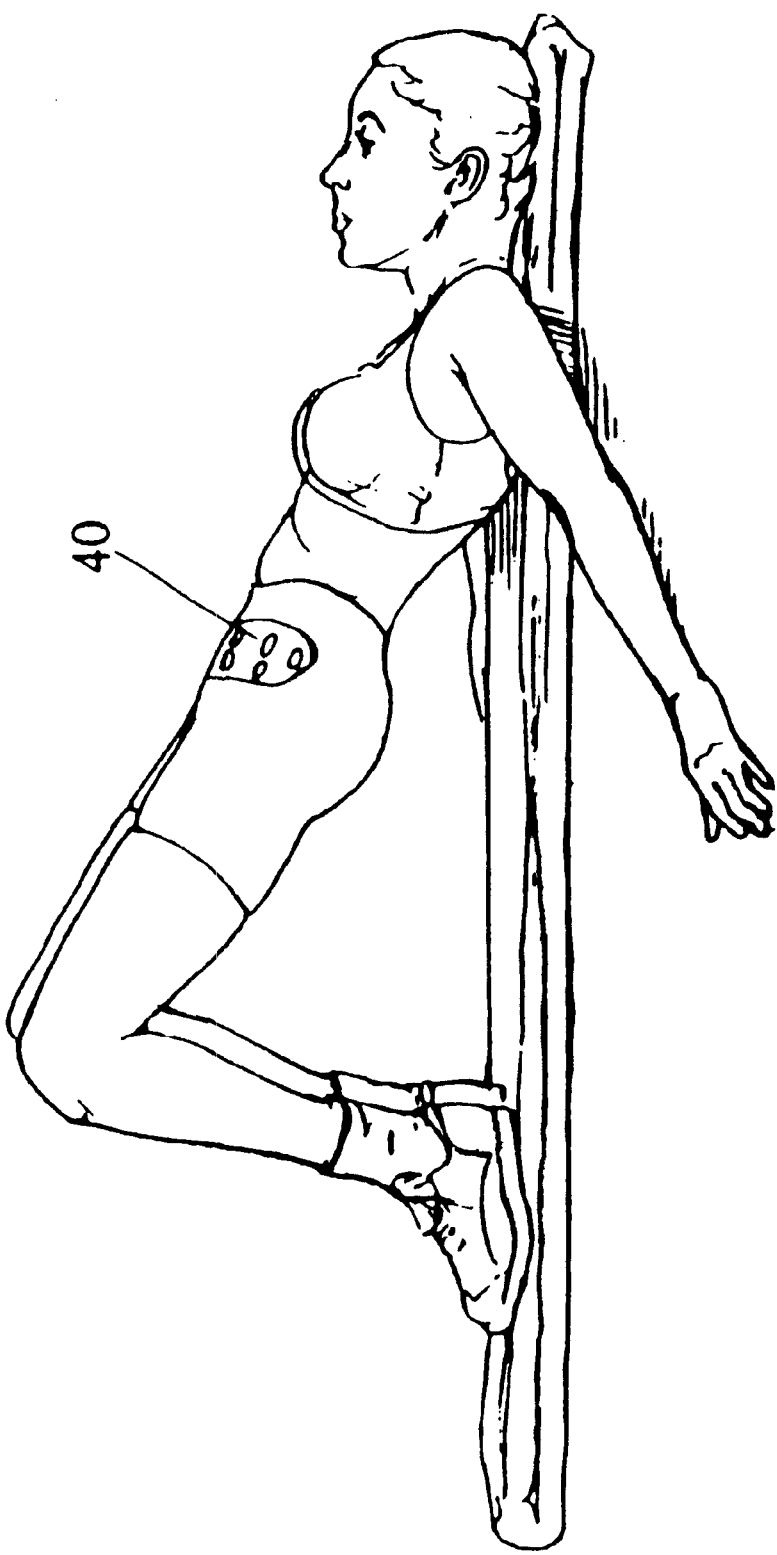

6. Lower Abdominal Strengthening–"The bridge" position (FIG. 34)

Starting position: lying on back on a flat horizontal surface, knees bent, feet and elbows on the flat horizontal surface.

a. Flatten lower back against the flat horizontal surface by tightening the muscles of abdomen and buttock.

b. Lift up hips and lower back to form a straight line from knees to chest.

c. Hold for 20 seconds, then slowly relax and return to starting position.

d. Repeat steps a–c two times for a total of three repetitions.

Methods of Treating Pain

The present invention further includes methods of treating pain comprising maintaining a sustained skin temperature of from about 32° C. to about 50° C., preferably from about 32° C. to about 45° C., more preferably from about 32° C. to about 42° C., most preferably from about 32° C. to about 40° C., to the specific areas of the body of a human or animal suffering acute, recurrent, and/or chronic pain, by application of topical heat to the afflicted body part of a human or animal suffering such pain, for from about fifteen minutes to about three hours, preferably from about thirty minutes to about four hours, more preferably from about forty-five minutes to about six hours, most preferably from about one hour to about eight hours while performing the above-described therapeutic exercise(s). Preferably the methods of the present invention include application of the above-described topical heat to the afflicted body part of a human or animal suffering such pain from about thirty minutes to about six hours before starting the above-described therapeutic exercise or exercises, more preferably from about forty-five minutes to about four hours before starting the above-described therapeutic exercise or exercises, most preferably from about one hour to about three hours before starting the above-described therapeutic exercise or exercises, to the completion of the exercise or exercises. More preferably the methods of the present invention include application of the above-described topical heat to the afflicted body part of a human suffering such pain from about thirty minutes to about six hours before starting the above-described therapeutic exercise or exercises, more preferably from about forty-five minutes to about four hours before starting the above-described therapeutic exercise or exercises, most preferably from about one hour to about three hours before starting the above-described therapeutic exercise or exercises, to from about one hour to about six hours after completion of the above-described therapeutic exercise or exercises.

Preferably the method includes maintaining a sustained skin temperature to the body of a human or animal having acute, recurrent, and/or chronic pain, of from about 32° C. to about 40° C., for a time period of about 2 hours before starting the above-described therapeutic exercise or exercises, during performing the appropriate above-described therapeutic exercise or exercises for the specific afflicted body part, to from about one hour to about three hours after completion of the above-described therapeutic exercise or exercises, to substantially relieve acute, recurrent, and/or chronic pain, including skeletal, muscular, and/or referred body pain of a human having such pain.

More preferably the method includes maintaining a sustained skin temperature to the body of a human having acute, recurrent, and/or chronic pain, of from about 32° C. to about 40° C., by wearing a portable, thermal wrap, such as ThermaCare® HeatWrap, appropriately selected for the specific afflicted body part, for a time period of about 2 hours before starting the above-described therapeutic exercise or exercises, during performing the appropriate above-described therapeutic exercise or exercises for the specific afflicted body part, to from about one hour to about three hours after completion of the above-described therapeutic exercise or exercises, to substantially relieve acute, recurrent, and/or chronic pain, including skeletal, muscular, and/or referred body pain of a human having such pain.

Typically a human having such pain will achieve substantially prolonged relief from acute, recurrent, and/or chronic pain for at least about 2 hours, even after the above-described therapeutic exercise or exercises are completed and the heat source is removed from the afflicted body part of the user.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Example 1

A woman suffering from acute neck and/or upper back pain places a portable, thermal neck wrap (ThermaCare® HeatWrap for the neck) around her neck and securely fastens it in place for about 2 hours before beginning the Exercises for Neck Pain. After about 2 hours the woman performs the Postural Exercise, Neck Flexibility Exercises, and Neck Strengthening Exercises as described in the set of instructions printed on a brochure and placed inside the container with the thermal neck wrap. After completion of the exercises the woman keeps the thermal neck wrap in place around her neck for about 1 hour after completing the exercises.

Example 2

A man suffering from chronic lower back pain places a portable, thermal back wrap (ThermaCare® HeatWrap for the back) around his torso and securely fastens it in place for about 2 hours before beginning the Exercises for Lower Back Pain. After about 2 hours the man performs the Low Back Mobility Exercises as described in the set of instructions printed on the container containing the thermal back wrap. After completion of the exercises the man keeps the thermal back wrap in place around his torso for about 4 hours after completing the exercises.

Example 3

A man suffering from acute pain in the left knee places a portable, thermal knee wrap (ThermaCare® HeatWrap for the knee) around his left knee and securely fastens it in place for about 2 hours before beginning the Exercises for Knee Pain. After about 2 hours the man performs the Knee/Leg Flexibility Exercises and Knee/Leg Strengthening Exercises as described in the set of instructions printed on a brochure and placed inside the container with the thermal knee wrap. After completion of the exercises the man keeps the thermal knee wrap in place around his left knee for about 5 hours after completing the exercises.

Example 4

A woman suffering from acute abdominal (menstrual) pain placs a portable, thermal body patch (ThermaCare® HeatWrap patch) on her abdomen and securely fastens it in place for about 4 hours before beginning the Exercises for Abdominal Pain. After about 4 hours the woman performs the Abdominal Stretching Exercises as described in the set of instructions printed on the thermal body patch. After completion of the exercises the woman keeps the thermal body patch in place on her abdomen for about 3 hour after completing the exercises.

What is claimed is:

1. An article of manufacture for treating pain and increasing tissue healing and rehabilitation in a human or animal afflicted with injury and/or inflammation of the muscle and/or joints and/or skeletal system, comprising:
   a) a portable, topical heat source having conformity with the body and/or body part of said human or animal afflicted with said injury and/or inflammation without substantially hindering movement of said body and/or body part of said human or animal;

b) a set of instructions in association with said topical heat source comprising the instructions for performing a therapeutic exercise or set of therapeutic exercises designed to develop or restore strength, endurance, and/or function to said body or body part of said human or animal afflicted with said injury and/or inflammation; and c) a container for containing said topical heat source and said set of instructions prior to applying said topical heat source to said body and/or body part of said human or animal and performing said therapeutic exercise or set of therapeutic exercises to develop or restore strength, endurance, and/or function to said body or body part of said human or animal.

2. An article of manufacture according to claim 1 wherein said topical heat source is selected from the group consisting of hot towels, hot water bottles, hot packs, hand warmers, heating pads, heating patches, and heat wraps.

3. An article of manufacture according to claim 2 wherein said topical heat source is selected from the group consisting of heating patches, heat wraps, hot packs, and hand warmers.

4. An article of manufacture according to claim 1 wherein said set of instructions is selected from the group consisting of a brochure, print advertisement, printed directly on said topical heat source, printed directly on said container, and mixtures thereof, wherein said brochure, print advertisement, or direct printing comprises instructions to perform said therapeutic exercise or set of exercises, appropriate for the specific afflicted body part, or instructions directing the consumer to dial a specific telephone number wherein instructions to perform said therapeutic exercise or set of exercises, appropriate for the specific afflicted body part, are presented by verbal communication, or instructions directing the consumer to a specific computer internet website wherein the instructions to perform said therapeutic exercise or set of exercises, appropriate for the specific afflicted body part, are displayed as an electronic advertisement.

5. An article of manufacture according to claim 3 wherein said topical heat source is selected from the group consisting of heating patches and heat wraps.

6. An article of manufacture according to claim 1 wherein said therapeutic exercise or set of exercises is designed to develop or restore strength, endurance, and/or function to the body or body part selected from the group consisting of the neck, upper back, lower back, knee, abdomen, and combinations thereof.

7. An article of manufacture according to claim 6 wherein said therapeutic exercise or set of exercises designed to develop or restore strength, endurance, and/or function to the neck is selected from the group consisting of chin tuck, head rotation, flexing and/or extending the neck, side bending stretch of the neck, chest and/or shoulder stretch, shoulder squeeze, resisted side bend of the neck, alternate resisted side bend of the neck, resisted flexion of the neck, alternate resisted flexion of the neck, resisted extension of the neck, alternate resisted extension of the neck, and combinations thereof.

8. An article of manufacture according to claim 6 wherein said therapeutic exercise or set of exercises designed to develop or restore strength, endurance, and/or function to the lower back is selected from the group consisting of cat stretch, full press extension, partial press extension, standing extension, side stretch, hip stretch, hamstring stretch, lower trunk rotation, pelvic tilt, lower abdominal strengthening, and combinations thereof.

9. An article of manufacture according to claim 6 wherein said therapeutic exercise or set of exercises designed to develop or restore strength, endurance, and/or function to the knee is selected from the group consisting of standing quadriceps stretch, reclining quadriceps stretch, calf muscle stretch, reclining hamstring stretch, sitting hamstring stretch, vertical squat, standing squat, leg lift, and combinations thereof.

10. An article of manufacture according to claim 6 wherein said therapeutic exercise or set of exercises designed to develop or restore strength, endurance, and/or function to the abdomen is selected from the group consisting of cat stretch, lower trunk rotation, buttock and/or hip stretch, pelvic tilt, lower abdominal strengthening, and combinations thereof.

11. An article of manufacture according to claim 1 wherein said container is selected from the group consisting of boxes, bags, envelops, pouches, bottles, jars, cartons, packets, and mixtures thereof.

12. An article of manufacture according to claim 11 wherein said container is selected from the group consisting of boxes, bags, pouches, packets, and mixtures thereof.

13. An article of manufacture according to claim 12 wherein said container is selected from the group consisting of boxes, bags, and mixtures thereof.

14. An article of manufacture according to claim 6 wherein said therapeutic exercise or set of exercises is designed to develop or restore strength, endurance, and/or function to the body or body part selected from the group consisting of the neck, upper back, lower back, knee, abdomen, and combinations thereof.

15. An article of manufacture according to claim 14 wherein said therapeutic exercise or set of exercises designed to develop or restore strength, endurance, and/or function to the neck is selected from the group consisting of chin tuck, head rotation, flexing and/or extending the neck, side bending stretch of the neck, chest and/or shoulder stretch, shoulder squeeze, resisted side bend of the neck, alternate resisted side bend of the neck, resisted flexion of the neck, alternate resisted flexion of the neck, resisted extension of the neck, alternate resisted extension of the neck, and combinations thereof.

16. An article of manufacture according to claim 14 wherein said therapeutic exercise or set of exercises designed to develop or restore strength, endurance, and/or function to the lower back is selected from the group consisting of cat stretch, full press extension, partial press extension, standing extension, side stretch, hip stretch, hamstring stretch, lower trunk rotation, pelvic tilt, lower abdominal strengthening, and combinations thereof.

17. An article of manufacture according to claim 14 wherein said therapeutic exercise or set of exercises designed to develop or restore strength, endurance, and/or function to the knee is selected from the group consisting of standing quadriceps stretch, reclining quadriceps stretch, calf muscle stretch, reclining hamstring stretch, sitting hamstring stretch, vertical squat, standing squat, leg lift, and combinations thereof.

18. An article of manufacture according to claim 14 wherein said therapeutic exercise or set of exercises designed to develop or restore strength, endurance, and/or function to the abdomen is selected from the group consisting of cat stretch, lower trunk rotation, buttock and/or hip stretch, pelvic tilt, lower abdominal strengthening, and combinations thereof.

19. A method of treating pain and increasing tissue healing and rehabilitation in a human or animal afflicted with injury and/or inflammation of the muscle and/or joints and/or skeletal system, comprising the steps of:

a) applying a portable, topical heat source having conformity with the body and/or body part of said human or animal afflicted with said injury and/or inflammation without substantially hindering movement of said body and/or body part of said human or animal, wherein a skin temperature of from about 32° C. to about 50° C. is sustained to said afflicted body or body part of said human or animal for from about thirty minutes to about six hours prior to performing a therapeutic exercise or set of therapeutic exercises designed to develop or restore strength, endurance, and/or function to said body or body part of said human or animal afflicted with said injury and/or inflammation; and b) performing said therapeutic exercise or set of therapeutic exercises while applying said topical heat source to maintain said skin temperature through completion of said therapeutic exercise or set of therapeutic exercises.

20. A method according to claim 19 wherein said therapeutic exercise or set of exercises is designed to develop or restore strength, endurance, and/or function to the body or body part selected from the group consisting of the neck, upper back, lower back, knee, abdomen, and combinations thereof.

21. A method according to claim 20 wherein said therapeutic exercise or set of exercises designed to develop or restore strength, endurance, and/or function to the neck is selected from the group consisting of chin tuck, head rotation, flexing and/or extending the neck, side bending stretch of the neck, chest and/or shoulder stretch, shoulder squeeze, resisted side bend of the neck, alternate resisted side bend of the neck, resisted flexion of the neck, alternate resisted flexion of the neck, resisted extension of the neck, alternate resisted extension of the neck, and combinations thereof.

22. A method according to claim 20 wherein said therapeutic exercise or set of exercises designed to develop or restore strength, endurance, and/or function to the lower back is selected from the group consisting of cat stretch, full press extension, partial press extension, standing extension, side stretch, hip stretch, hamstring stretch, lower trunk rotation, pelvic tilt, lower abdominal strengthening, and combinations thereof.

23. A method according to claim 20 wherein said therapeutic exercise or set of exercises designed to develop or restore strength, endurance, and/or function to the knee is selected from the group consisting of standing quadriceps stretch, reclining quadriceps stretch, calf muscle stretch, reclining hamstring stretch, sitting hamstring stretch, vertical squat, standing squat, leg lift, and combinations thereof.

24. A method according to claim 20 wherein said therapeutic exercise or set of exercises designed to develop or restore strength, endurance, and/or function to the abdomen is selected from the group consisting of cat stretch, lower trunk rotation, buttock and/or hip stretch, pelvic tilt, lower abdominal strengthening, and combinations thereof.

* * * * *